United States Patent
Cahill

(10) Patent No.: US 8,992,545 B2
(45) Date of Patent: Mar. 31, 2015

(54) IMPLANT-CATHETER ATTACHMENT MECHANISM USING SNARE AND METHOD OF USE

(75) Inventor: Ryan Cahill, Brighton, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1501 days.

(21) Appl. No.: 11/904,545

(22) Filed: Sep. 27, 2007

(65) Prior Publication Data

US 2008/0086168 A1    Apr. 10, 2008

Related U.S. Application Data

(60) Provisional application No. 60/847,703, filed on Sep. 28, 2006.

(51) Int. Cl.
  *A61F 11/00* (2006.01)
  *A61B 17/00* (2006.01)

(52) U.S. Cl.
  CPC ... *A61B 17/0057* (2013.01); *A61B 2017/00575* (2013.01); *A61B 2017/00592* (2013.01); *A61B 2017/00606* (2013.01); *A61B 2017/00619* (2013.01); *A61B 2017/00623* (2013.01); *A61B 2017/00867* (2013.01)
  USPC .......................................... 606/108; 606/213

(58) Field of Classification Search
  USPC .......... 606/208, 113, 151, 213, 108; 623/1.11
  See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,699,611 A | 10/1987 | Bowden |
| 4,704,131 A | 11/1987 | Noishiki et al. |
| 4,710,192 A | 12/1987 | Liotta et al. |
| 4,836,204 A | 6/1989 | Landymore et al. |
| 4,917,089 A | 4/1990 | Sideris |
| 4,946,440 A | 8/1990 | Hall |
| 5,098,440 A * | 3/1992 | Hillstead ................ 606/108 |
| 5,108,420 A | 4/1992 | Marks |
| 5,171,259 A | 12/1992 | Inoue |
| 5,192,301 A | 3/1993 | Kamiya et al. |
| 5,222,974 A | 6/1993 | Kensey et al. |
| 5,282,827 A | 2/1994 | Kensey et al. |
| 5,284,488 A | 2/1994 | Sideris |
| 5,312,435 A | 5/1994 | Nash et al. |
| 5,350,399 A | 9/1994 | Erlebacher et al. |
| 5,433,727 A | 7/1995 | Sideris |
| 5,437,288 A | 8/1995 | Schwartz et al. |
| 5,620,461 A | 4/1997 | Muijs Van De Moer et al. |
| 5,634,936 A | 6/1997 | Linden et al. |

(Continued)

*Primary Examiner* — Dianne Dornbusch
(74) *Attorney, Agent, or Firm* — DLA Piper LLP (US)

(57) ABSTRACT

Devices, delivery systems and delivery techniques for an occlusion device for the closure of physical anomalies, such as an atrial septal defect, a patent foramen ovale (PFO), and other septal and vascular defects are described. The devices, delivery systems and delivery techniques relate particularly to, but are not limited to, a patent foramen ovale (PFO) occluder made from a polymer tube. The securement systems enable the deployment (and retrieval) of the device. In one aspect, the second securement system employs a snare connection. The snare connection may have various configurations, including a single snare, double snare, and double criss-cross snare. The securement systems are detached when the device has been properly positioned. The securement systems can be manipulated by control systems provided in the control portion of the delivery system.

9 Claims, 31 Drawing Sheets

(56) References Cited

U.S. PATENT DOCUMENTS

| | | |
|---|---|---|
| 5,649,959 A | 7/1997 | Hannam et al. |
| 5,690,674 A | 11/1997 | Diaz |
| 5,709,707 A | 1/1998 | Lock et al. |
| 5,713,948 A * | 2/1998 | Uflacker ............... 623/1.23 |
| 5,725,553 A | 3/1998 | Moenning |
| 5,853,420 A | 12/1998 | Chevillon et al. |
| 5,853,422 A | 12/1998 | Huebsch et al. |
| 5,861,003 A | 1/1999 | Latson et al. |
| 5,879,366 A | 3/1999 | Shaw et al. |
| 5,967,490 A | 10/1999 | Pike |
| 6,024,756 A | 2/2000 | Huebsch et al. |
| 6,080,182 A | 6/2000 | Shaw et al. |
| 6,117,159 A | 9/2000 | Huebsch et al. |
| 6,171,329 B1 | 1/2001 | Shaw et al. |
| 6,261,309 B1 | 7/2001 | Urbanski |
| 6,312,446 B1 | 11/2001 | Huebsch et al. |
| 6,344,048 B1 | 2/2002 | Chin et al. |
| 6,623,508 B2 | 9/2003 | Shaw et al. |
| 7,678,123 B2 | 3/2010 | Chanduszko |
| 2002/0095174 A1 | 7/2002 | Tsugita et al. |
| 2002/0183787 A1 | 12/2002 | Wahr et al. |
| 2002/0198563 A1 * | 12/2002 | Gainor et al. ............... 606/213 |
| 2003/0050665 A1 | 3/2003 | Ginn |
| 2003/0055455 A1 | 3/2003 | Yang et al. |
| 2004/0006330 A1 | 1/2004 | Fangrow |
| 2004/0073242 A1 | 4/2004 | Chanduszko |
| 2005/0267523 A1 | 12/2005 | Devellian et al. |
| 2005/0267563 A1 | 12/2005 | Case et al. |
| 2005/0273135 A1 | 12/2005 | Chanduszko et al. |
| 2006/0122647 A1 | 6/2006 | Callaghan et al. |
| 2006/0265004 A1 | 11/2006 | Callaghan et al. |
| 2007/0010851 A1 | 1/2007 | Chanduszko et al. |
| 2007/0167981 A1 | 7/2007 | Opolski et al. |
| 2007/0179474 A1 | 8/2007 | Cahill et al. |
| 2007/0244517 A1 | 10/2007 | Callaghan |
| 2007/0244518 A1 | 10/2007 | Callaghan |
| 2007/0250081 A1 | 10/2007 | Cahill et al. |
| 2007/0250115 A1 | 10/2007 | Opolski et al. |
| 2007/0276415 A1 | 11/2007 | Kladakis et al. |
| 2007/0282430 A1 | 12/2007 | Thommen et al. |
| 2008/0077180 A1 | 3/2008 | Kladakis et al. |
| 2008/0086168 A1 | 4/2008 | Cahill |
| 2008/0091234 A1 | 4/2008 | Kladakis |
| 2008/0249562 A1 | 10/2008 | Cahill |
| 2009/0088795 A1 | 4/2009 | Cahill |
| 2010/0145382 A1 | 6/2010 | Chanduszko |

* cited by examiner

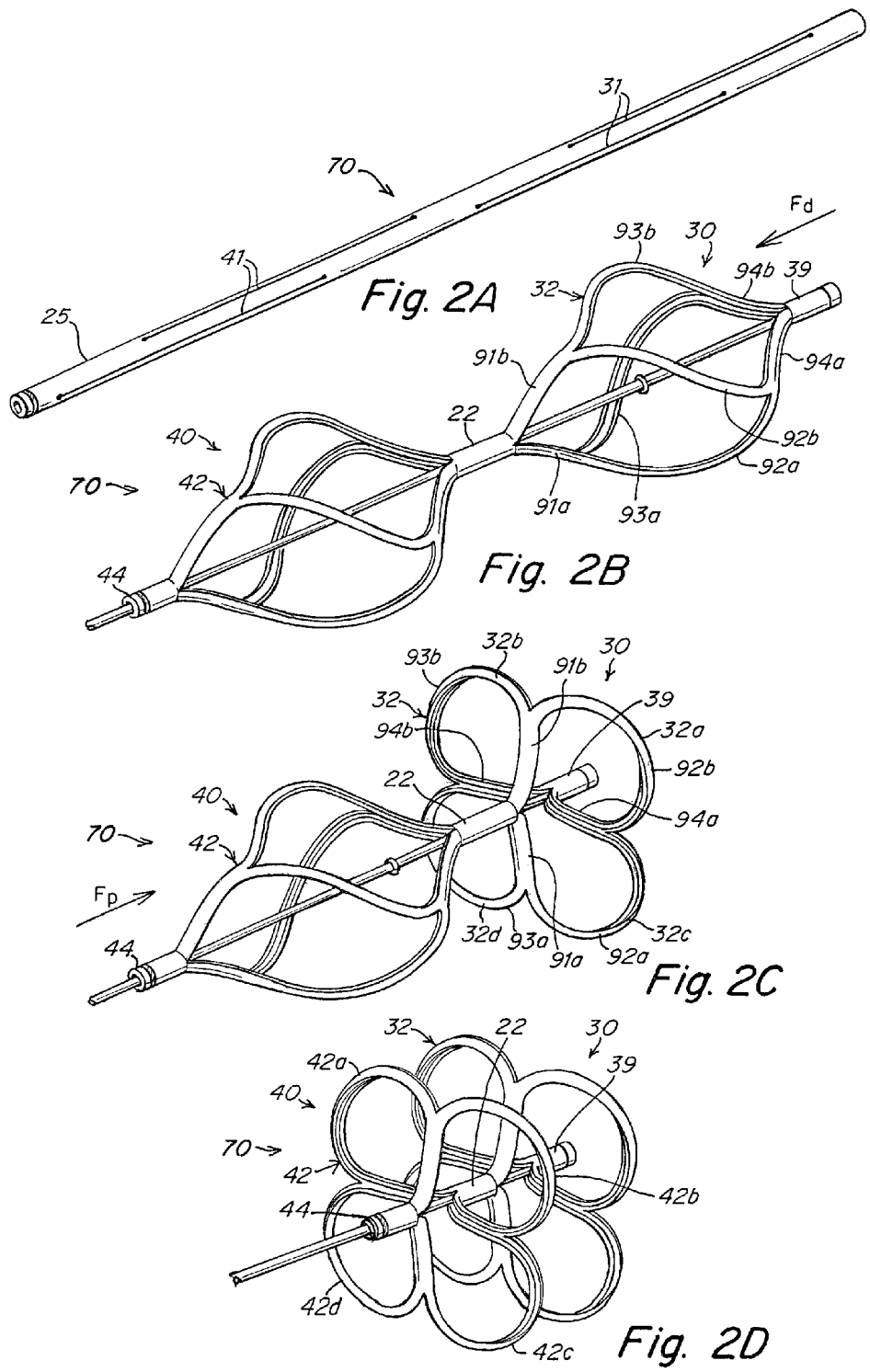

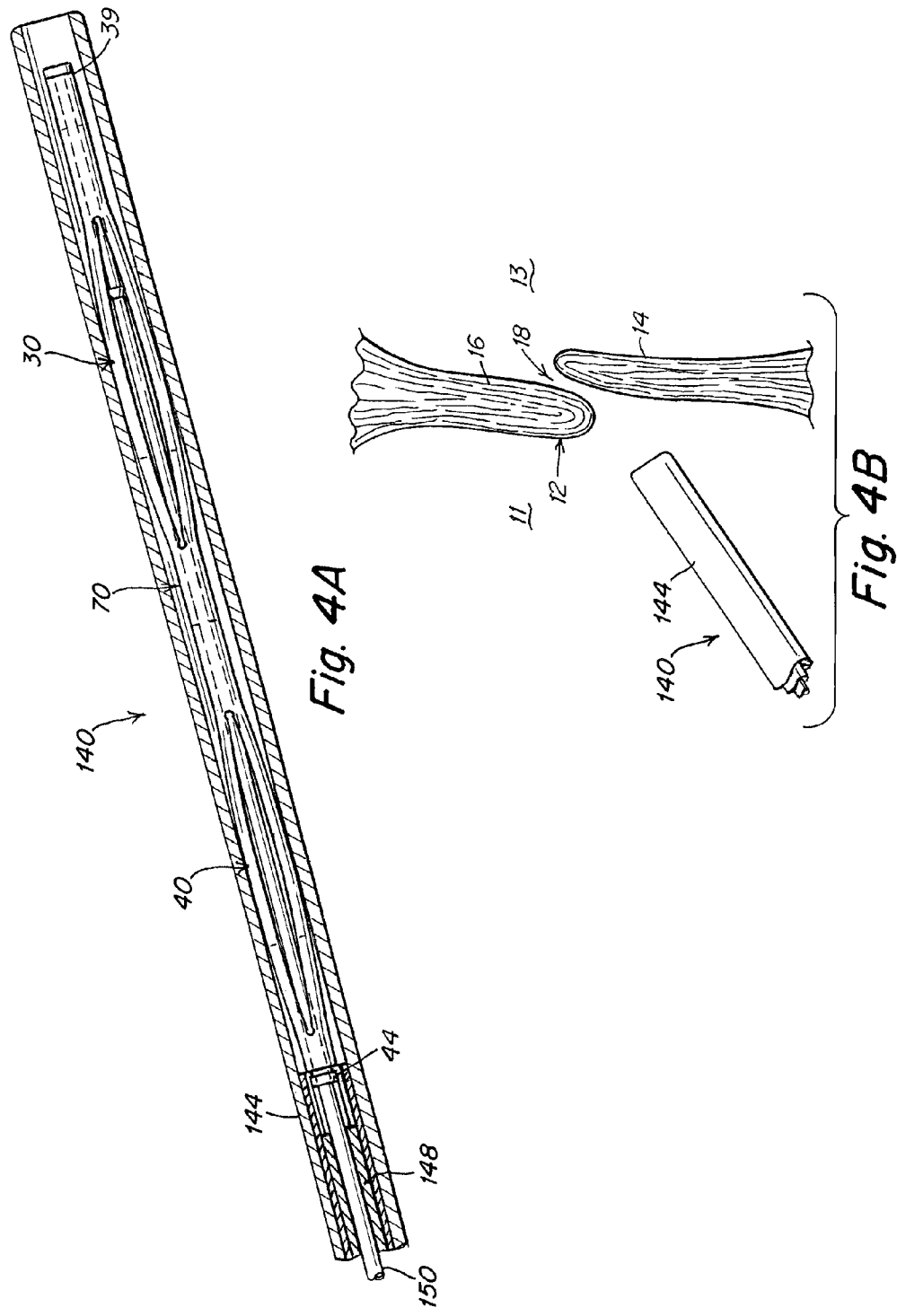

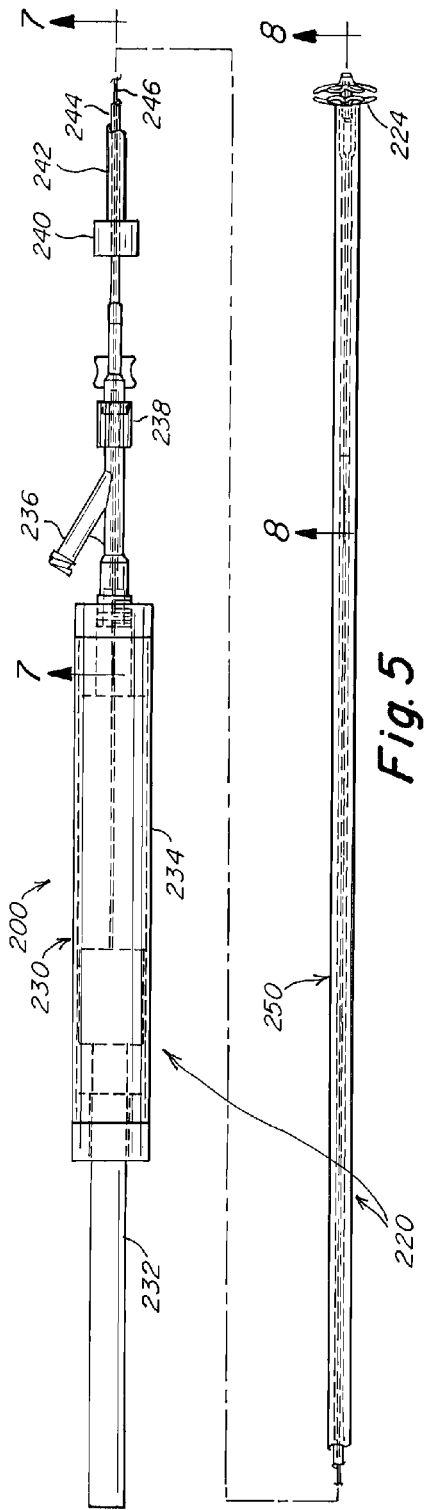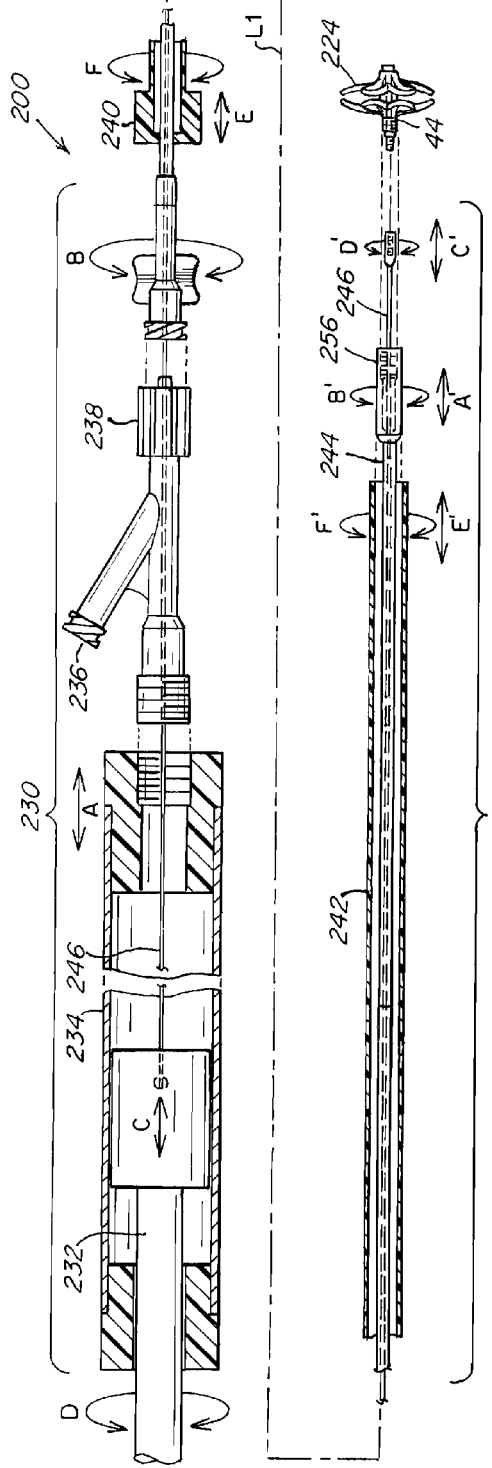

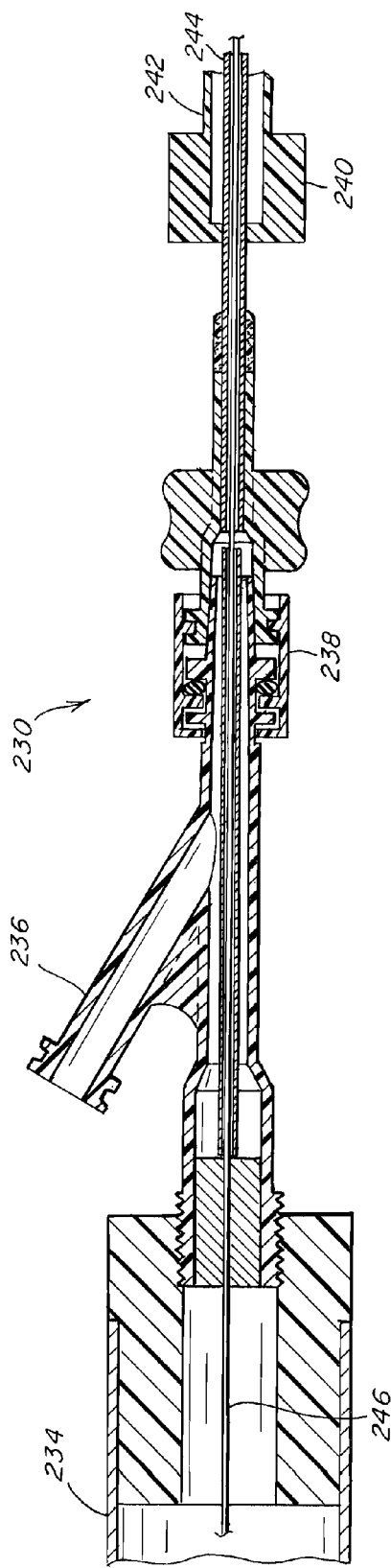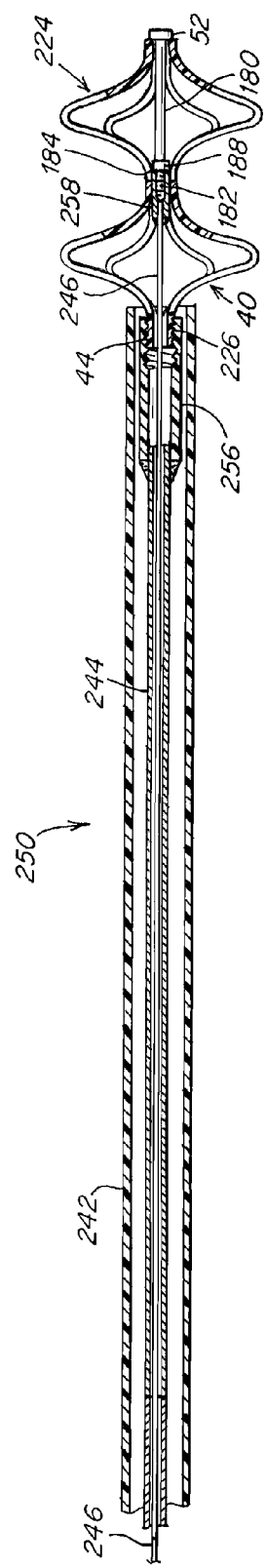

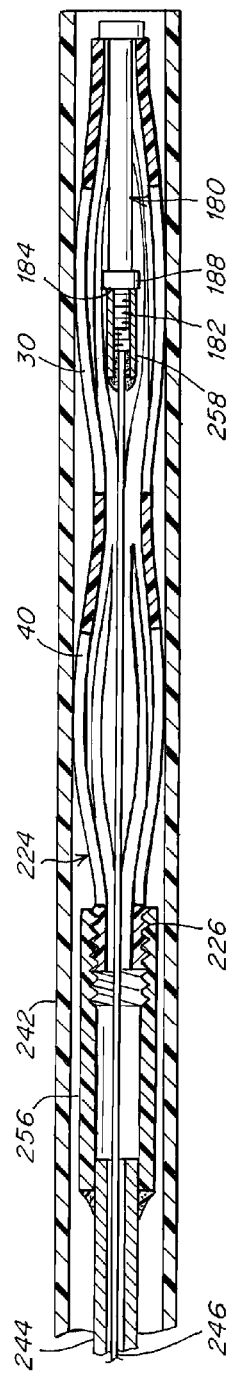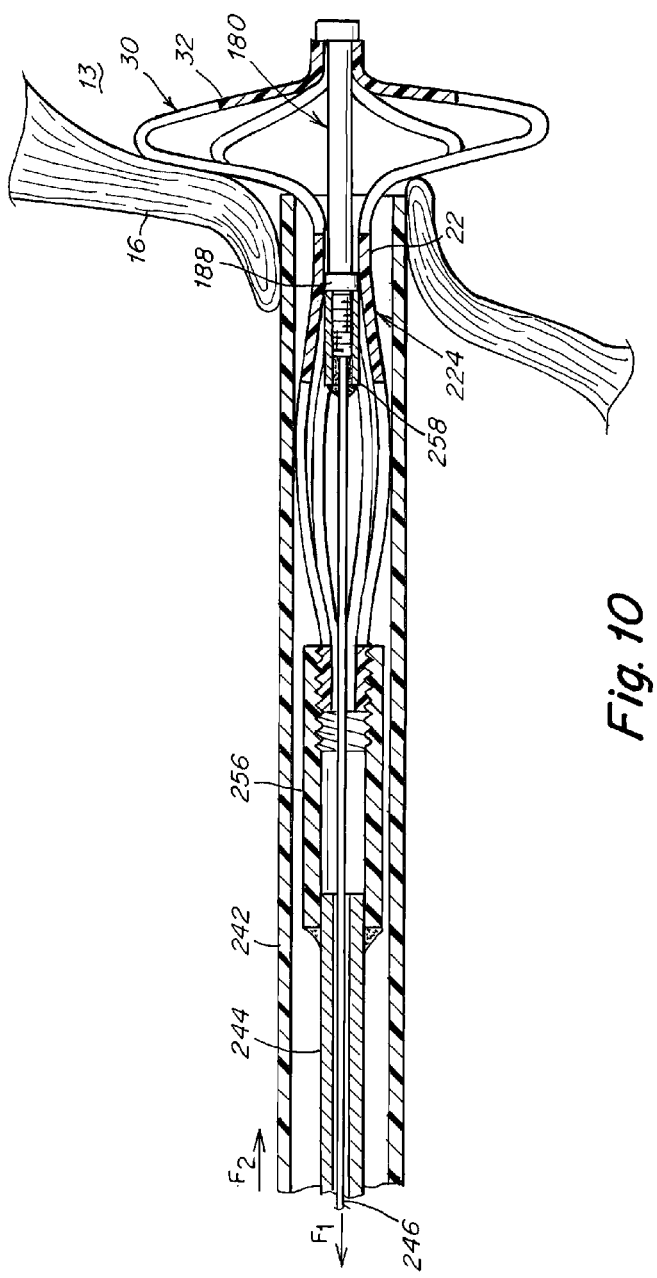
Fig. 9
Fig. 10

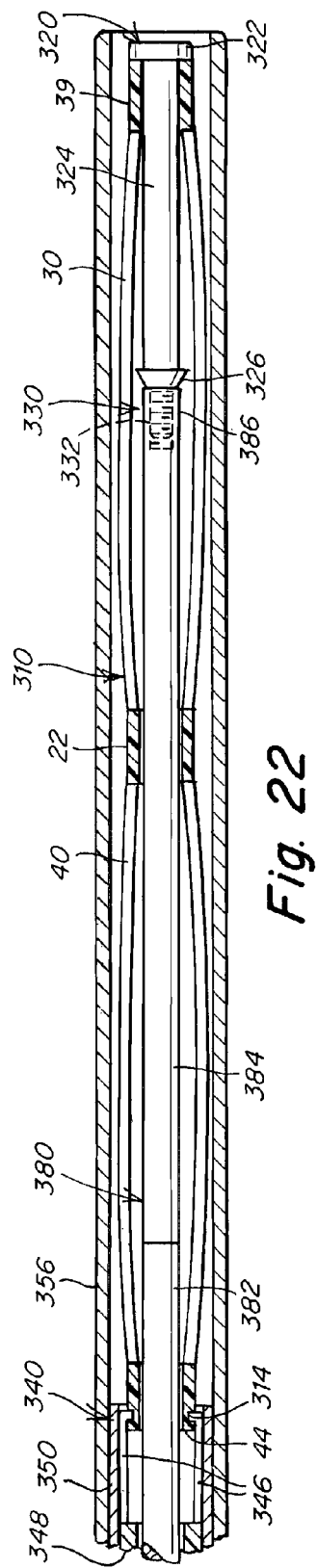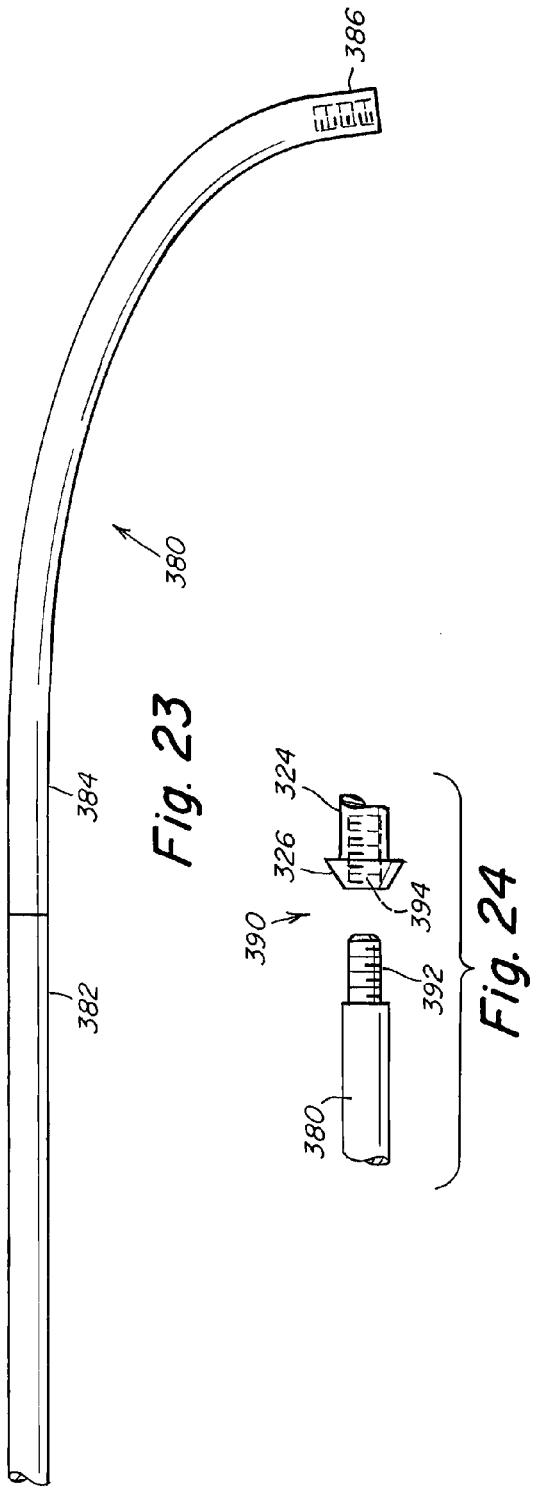

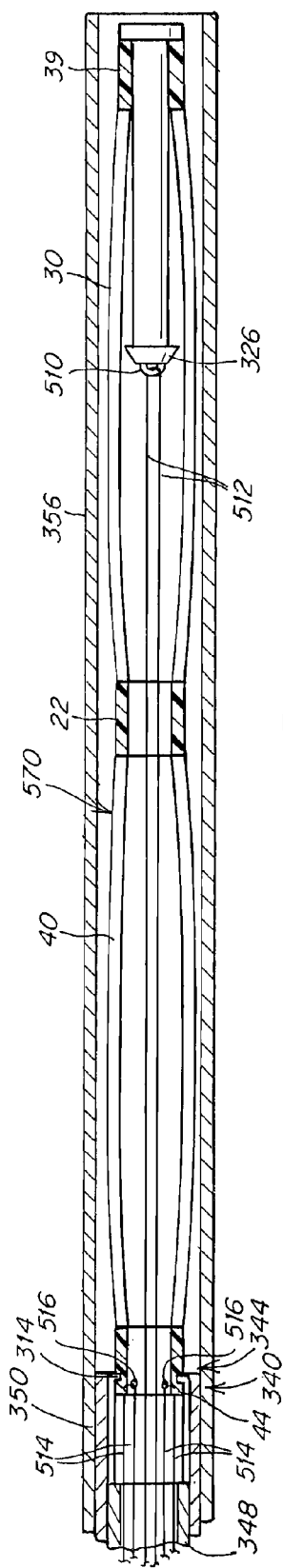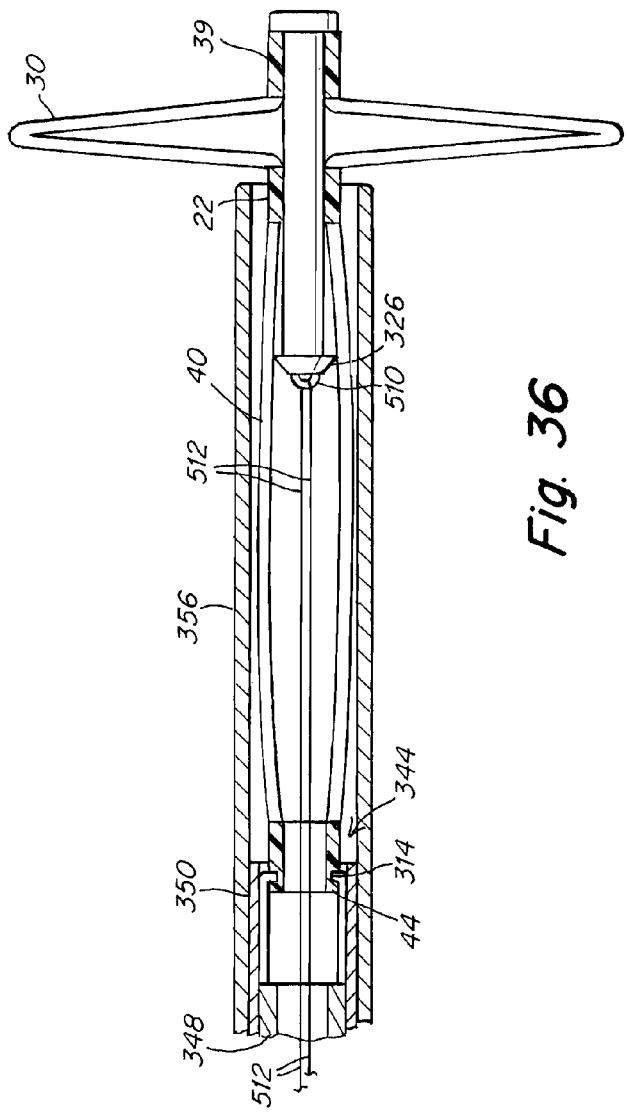
Fig. 35
Fig. 36

US 8,992,545 B2

IMPLANT-CATHETER ATTACHMENT MECHANISM USING SNARE AND METHOD OF USE

CROSS REFERENCE TO RELATED APPLICATIONS

This application claims the benefit of provisional application U.S. Ser. No. 60/847,703 filed Sep. 28, 2006, the contents of which are incorporated by reference.

TECHNICAL FIELD

This invention relates generally to occlusion devices for the closure of physical anomalies, such as an atrial septal defect, a patent foramen ovale, and other septal and vascular defects. The invention also relates to delivery systems and mechanisms for such devices.

BACKGROUND

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various delivery systems have been used to deliver occluders and other medical devices through body lumens. Some delivery systems of the prior art are used to deliver devices that readily expand to a deployed configuration when removed from the delivery system. Such delivery systems are not generally suited for delivering a device that does not readily expand into the deployed configuration. Further, the delivery systems of the prior art may not allow verification of the position of the device prior to full deployment of the device. Finally delivery systems of the prior art may not be suitable to manipulate the configuration of the device in a secure manner to allow for complete deployment of the device.

The devices and techniques disclosed herein are designed to address these and other deficiencies of prior art septal closure devices and techniques for delivering and retrieving such devices.

SUMMARY OF THE INVENTION

These and other aspects and embodiments of the disclosure are illustrated and described below.

This description discloses several delivery devices and techniques for delivering an implant into a desired location within the body. This delivery technique relates particularly to, but is not limited to, a septal occluder made from a polymer tube. These delivery techniques, in addition to use with septal occluders, could be applied to other medical devices, such as other expandable devices constructed from an underlying tubular structure.

In one aspect, a delivery system is disclosed for delivering an occluder that closes an aperture in septal tissue. The occluder includes a first side adapted to be disposed on one side of the septal tissue and a second side adapted to be disposed on the opposite side of the septum. The first and second sides are adapted to occlude the aperture upon deployment of the device at its intended delivery location. The device also includes a catch system that maintains the configuration of the device once it has been deployed.

According to at least some embodiments, the device is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the device is formed by cutting the tube. The device is placed in its deployment configuration by reducing the axial length of the device.

According to some embodiments, the catch system reduces and maintains the axial length of the device. Also, varied constructions could be used to maintain the axial dimension of the device. In one form, catch elements such as, for example, balls, attached to a delivery wire could be used to maintain the axial dimension of the device. In a different construction, a locking mechanism could be used. Preferably, if a locking mechanism is used, it secures both sides of the device in the locked position with a single locking element. In some embodiments, a catch element secures the ends of the occluder in a compressed position. Preferably, if a catch mechanism is used, it secures both sides of the device in the deployed position with a single element.

In another aspect, the present invention provides a device for occluding an aperture in septum, including a first side adapted to be disposed on one side of the septum and a second side adapted to be disposed on the opposite side of the septum. The first and second sides are adapted to occlude the defect when the device is deployed at its intended delivery location. Each of the first and second sides includes loops. The device further includes a catch system that maintains the configuration of the device once it has been deployed. The loops of the first and second sides and the catch system cooperate to provide a compressive force to the septum surrounding the aperture.

According to some embodiments, each of the first and second sides includes at least two loops. In particular embodiments, each of the first and second sides includes four or six loops. Of course, the most desirable number of loops on each side will depend on a variety of anatomical and manufacturing factors. According to some embodiments, the device also includes a central tube that connects the first and second sides.

The delivery system may be used to deliver an occluder in which at least one of the first and second sides further includes a tissue scaffold. The tissue scaffold includes a material selected from the group consisting of polyester fabrics, Teflon-based materials, polyurethanes, metals, polyvinyl alcohol (PVA), extracellular matrix (ECM) or other bioengineered materials, synthetic bioabsorbable polymeric scaffolds, collagen, and combinations thereof. In particular embodiments, the tissue scaffold includes nitinol.

The delivery system includes a first and a second securement system, typically one for each end of the occluder. The first securement system may be used to secure the distal end of the occluder onto the delivery system. The first securement system may be any one of a number of configurations. First, a delivery wire may be used to secure the distal end of the occluder onto the delivery system. When a delivery wire is used, the distal end of the delivery wire may be threaded and cooperate with a corresponding threaded portion on the occluder or catch element. In a preferred form, the threaded portion may have male threads on the occluder and female threads on the delivery wire. The first securement system may also incorporate threads to catch the distal end of the occluder and a key/slot connection to permit rotation of the catch element. Alternatively, a ball and clasp, or other interlocking system may be used.

The second securement system may be used to secure the proximal end of the occluder onto the delivery system. The second securement system may be any one of a number of configurations. In one aspect it may be a threaded connection between the delivery system and the occluder. In another aspect, the second securement system is a collet system that includes fingers, which are configured to fit within a groove in the occluder and thus secure the occluder to the delivery system when the fingers are disposed in the groove. A collet sheath is moveable with respect to the fingers and when the collet fingers are disposed within the collet sheath, the fingers are configured to fit within the groove provided on the occluder.

In another aspect, a snare device provides the second securement system. The snare device includes a snare wire and the distal end of the snare device forms a loop that catches the proximal end of the occluder frame. The snare device is contained in a side lumen of the delivery system. The snare device can readily be released from the occluder frame by advancing the snare wire until the loop unhooks from the proximal end of the occluder frame. Alternatively, a coil-shaped snare may be used. In other embodiments, a double snare or criss-cross double snare may also be used.

In one aspect, a delivery system for the device is provided within (and includes) a delivery sheath. In certain embodiments, the delivery system includes a first securement system for securing a first end of the occluder and a second securement system for securing a second end of the occluder. The securement systems connect the occluder to first and second catheters contained in the delivery system and enable deployment and/or retrieval of the occluder. The catheters are preferably able to move relative to each other. The securement systems enable pushing and pulling of respective ends of the occluder to expand and contract the device. The first securement system may employ a threaded connection and the second securement system may employ a suture connection. The securement systems are detached when the device has been properly positioned.

In a further aspect of the invention, the first securement system secures a distal end of the device and the second securement system secures a proximal end of the device. A first catheter connects to the first securement system and a second catheter connects to the second securement system. In certain embodiments, the second catheter encloses the first catheter in its central lumen. In one aspect, the device is deployed by inserting the delivery system, removing the sheath, expanding the petals of a distal portion of the device, and expanding the petals of a proximal portion of the device. The delivery system can be detached by detaching the first and second securement systems, e.g., by unscrewing the first securement system and by cutting and removing the sutures. In another aspect, the deployed device is retrieved by contracting the petals of a proximal portion of the device using the second catheter, advancing the sheath over a proximal portion of the device, contracting the petals of a distal portion of the device using the first catheter and advancing the sheath over the distal portion of the device. The occluder can then be repositioned or removed.

In another aspect, a delivery system is disclosed for delivering an occluder that closes an aperture in the septum. The occluder includes a first side adapted to be disposed on one side of the septum and a second side adapted to be disposed on the opposite side of the septum. The first and second sides are adapted to occlude the aperture upon deployment of the device at its intended delivery location. The device also employs a catch system that maintains the configuration of the device once it has been deployed. The occluder may be held in its deployment configuration by the catch element.

In one aspect, a delivery system for the device is provided within a delivery sheath. In certain embodiments, the delivery system includes a first securement system for securing a first end of the occluder and a second securement system for securing a second end of the occluder. The securement systems connect the occluder to first and second extrusions, e.g., a catheter or a wire, contained in the delivery system and enable deployment and/or recovery of the occluder. The extrusions are preferably able to move relative to each other. The securement systems enable pushing and pulling of respective ends of the occluder by manipulating the extrusions to expand and contract the device by varying its axial length. The first securement system may employ a threaded connection. The second securement system may also employ a threaded connection or a snare connection. The securement systems are detached when the device has been properly positioned. The securement systems can be manipulated by control systems provided in the control portion of the delivery system.

In one preferred embodiment, the invention provides a axially collapsible occluder, a means for collapsing and expanding the occluder by changing the distance between the distal and proximal ends of the occluder, and a means for keeping the axial distance between the proximal and distal ends of the occluder fixed after its deployment.

These and other aspects and embodiments of the disclosure are illustrated and described below.

BRIEF DESCRIPTION OF THE DRAWINGS

In the Drawings:

FIGS. 2A-2D are isometric views of an embodiment of an occluder for use with disclosed delivery systems and techniques;

FIGS. 4A-4D are side views of a delivery assembly for delivering an occluder to a septal defect according to an aspect of the disclosure;

FIG. 5 is a side elevational view of a delivery system attached to an occluder in deployed configuration according to an aspect of the disclosure;

FIG. 6 is an exploded cross-sectional side view of a delivery system attached to an occluder in deployed configuration according to an aspect of the disclosure;

FIG. 7 is an enlarged cross-sectional side view of the control portion of a delivery system according to an aspect of the disclosure;

FIG. 8 is an enlarged cross-sectional side view of the catheter portion of a delivery system attached to an occluder according to an aspect of the disclosure;

FIG. 9 is a cross-sectional side view of the catheter portion of the delivery system attached to a collapsed occluder according to an aspect of the disclosure;

FIG. 10 is a cross-sectional side view of one step in a deployment sequence according to an aspect of the disclosure;

FIG. 22 is an axial cross-sectional drawing of an occluder, in a delivery configuration, according to an embodiment of the disclosure;

FIG. 23 is a detail view of the delivery wire according to an aspect of one embodiment of the disclosure;

FIG. 24 is a configuration for a first securement system according to an embodiment of the disclosure;

FIGS. 35-38 are sectional views of an alternative delivery system according to an aspect of the disclosure;

DETAILED DESCRIPTION

The present disclosure provides devices, delivery/retrieval systems and techniques for delivering such devices intended to occlude an aperture within body tissue. In particular and as described in detail below, the described occluder may be used for closing an ASD, VSD or PFO in the atrial septum of a heart. Although the embodiments are described with reference to an ASD, VSD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, which are aspects of the present invention may also be used in connection with other types of devices besides an occluder, in particular, devices having tubular profiles.

Figure 1:
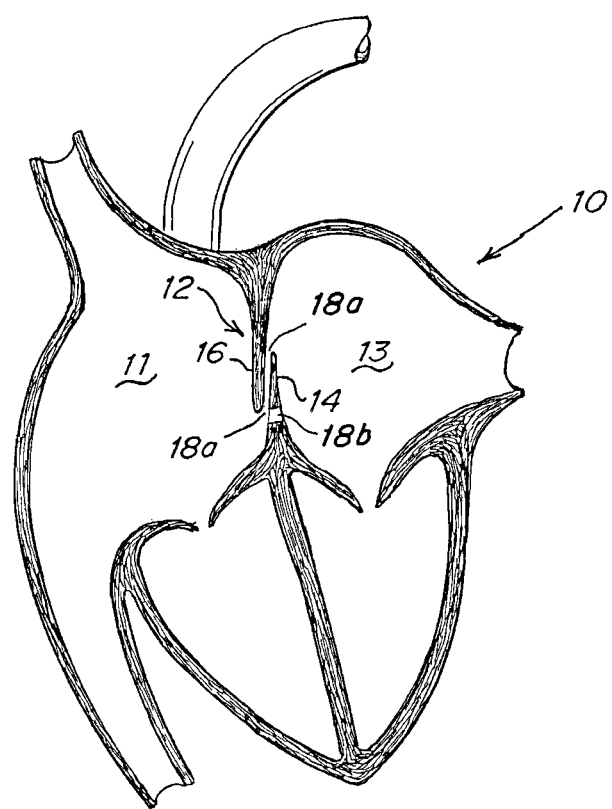
FIG. 1 is a schematic representation of a human heart including various septal defects.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally or alternatively, the presence of an ASD 18b could permit blood to travel through an aperture in the septum.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has deployed from the catheter, such as at the desired implantation location.

FIGS. 2A-D illustrates an exemplary occluder with which systems and techniques disclosed herein may be used. An occluder 70, for example, can be formed by cutting a series of slits on tube 25. As shown in FIGS. 2A-2D, distal petals 32 are produced by cutting slits 31 in the upper portion of tube 25 according to the cutting pattern shown in FIG. 2A. As shown in FIG. 2B, the distal portion of the tube 25 is cut in half to form half sections 91a and 91b. The half sections 91a and 91b are further cut to a proximal distance from distal tip 39 into quarter sections 92a, 93a, 92b, and 93b. The cuts are discontinued and quarter sections 92a and 92b form half section 94a at distal tip 39, and quarter sections 93a and 93b form half section 94b at distal tip 39. Upon application of force Fd to distal tip 39, struts defined by slits 31 bow and twist outward to form distal petals 32 in distal side 30, as shown in FIGS. 2C-2D. The movement of the struts during deployment is such that the struts rotate in an orthogonal plane relative to the axis of the device. Central tube 22 may be constrained during the application of force Fd, or any combination of forces sufficient to reduce the axial length of the tube 25 may be applied. One end of each of distal petals 32 originates from central tube 22, while the other end originates from distal tip 39 (FIGS. 2B-2C). Proximal petals 42 may be formed in proximal side 40, as shown in FIGS. 2B-2D, making slits 41 between central tube 22 and proximal end 44, using the same cutting pattern described above.

The tube(s) 25 forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The cross-sectional shape of tube 25 may be circular or polygonal, for example square, or hexagonal. The slits 31 and 41 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the struts could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

The petal configuration is the deployed configuration. The occluder 70 can be secured in the petal configuration by a catch system that holds the ends of the tube 25 together, certain embodiments of which are described below. Use of the terms distal and proximal sides or portions 30 and 40, respectively, include the petals that are formed on the distal and proximal sides.

The embodiment described in conjunction with FIGS. 2A-2D has similarities to the device disclosed in U.S. patent application Ser. No. 10/890,784, entitled Tubular Patent Foramen Ovale (PFO) Closure Device with Locking Mechanism, filed on Jul. 14, 2004; U.S. patent application Ser. No. 11/111, 685, entitled Closure Device with hinges, filed on Apr. 21, 2005; U.S. patent application Ser. No. 11/395,718, entitled Tubular Patent Foramen Ovale (PFO) Closure Device with Catch System, filed Mar. 31, 2006; U.S. patent application Ser. No. 11/729,636, entitled Adjustable Length Patent Foramen Ovale (PFO) Occluder and Catch System, filed Mar. 29, 2007; U.S. patent application Ser. No. 11/728,694, entitled Patent Foramen Ovale (PFO) Closure Device with Linearly Elongating Petals, filed Mar. 27, 2007; all of which have the same assignee as the present application, and are incorporated herein by reference in their entirety. These incorporated documents describe how a device can be formed by making cuts or slits in a tube and compressing the ends, and how to deliver such a device.

The transformable design of occluder 70 enables occluder 70 to be delivered in a low profile, tubular form and to be converted readily, i.e., by reducing the axial length, in place to the high-profile deployed configuration. Moreover, the conversion can readily be effected by forcing distal end 39 and proximal end 44 together. For example, distal side 30 and proximal side 40 of occluder 70 may be deployed in separate steps, or both distal side 30 and proximal side 40 of occluder 70 may be exposed (e.g., out of the delivery catheter) prior to engaging the catch system and deployed together as the catch element is engaged. Use of the terms distal and proximal side 30 and 40, respectively, include the loops or other geometries and configurations that are formed on the distal and proximal sides, respectively.

Occluder 70 may be prepared for delivery to an aperture 18 in any one of several ways. Slits 31 and 41 may be cut such that tube 25 bends into its intended configuration following deployment in vivo. Specifically, slits 31 and 41 may be cut to produce struts 32 and 42 of a thickness that facilitates the bending and formation of loops 32 and 42 upon the application of forces Fd and/or Fp during deployment. See FIGS. 2B and 2C. Alternatively and/or additionally, a tube 25 formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube 25 may be only slightly preformed ex vivo such that it is predisposed to bend into its intended shape in vivo upon application of forces Fd and Fp.

Figure 2E:
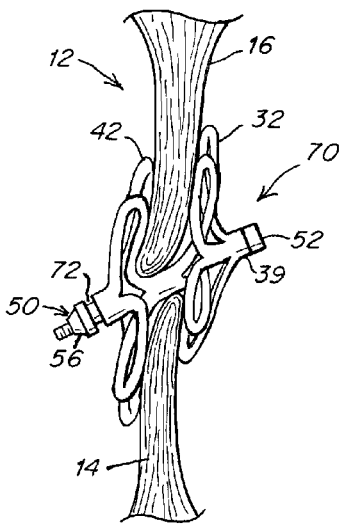
FIG. 2E illustrates a deployed occluder according to an aspect of the disclosure.

FIG. 2E shows a deployed occluder 70 in a human heart with a catch element 50 engaged. The term "catch system" describes the portion/aspect of the device that secures the device in the deployed configuration, it may be a single piece or a group of connected or assembled pieces. The catch element is the portion of the catch system that engages with the occluder to hold the occluder in the deployed configuration and is described in more detail below. The configuration illustrated is a simplified schematic view of the occluder 70 illustrated in FIGS. 2A-2D. This particular type of occluder 70 and catch element 50 are described for purposes of illustration and explanation; of course, other types of occluders (with different types of catch elements or systems) can be deployed using the catch systems described herein. The catch element 50, as illustrated, is disposed in an axially central location in the occluder 70 and is schematically illustrated as a separate piece than the occluder 70. In a preferred embodiment, the catch element may be fixed to one end of the tube 25 that forms occluder 70. For example, a flange 52 may be fixed to the distal tip 39 of the tube 25 that forms the distal and proximal petals 32 and 42.

In general, references to "occluder 70" herein may be inclusive of catch element 50, depending on the context, for example, unless separately listed or otherwise stated. One end of tube 25 is able to move with respect to the catch element 50 (and especially the catch system) so that the distal and proximal petals 32 and 42 can move from the delivery configuration to the deployed configuration. The inside surface of the tube 25 is able to slide over the catch element 50 so that, when the proximal end 44 of the occluder 70 rests against the surface of the proximal flange 56, the occluder 70 is secured in its deployed configuration. The catch element 50 is included in the catch system that includes a portion for connection to the delivery/recovery system, including, for example, a threaded section illustrated in FIG. 2E. The threaded section is an adaptation designed to fit with the desired type of securement system according to a preferred embodiment discussed herein and is not necessarily an inherent feature of the catch element 50. Occluder 70 also includes an additional feature, such as threads or a groove 72 (as illustrated) to provide another connection between the occluder and the delivery/recovery system.

Embodiments of catch systems, securement systems and other features described herein may also be used with tubular septal occluders having other shapes, such as those disclosed in U.S. patent application Ser. No. 11/121,833, entitled Locking Mechanisms for Tubular Septal Occluder, filed on May 4, 2005; U.S. patent application Ser. No. 11/384,635, entitled Catch member for PFO Occluder, filed on Mar. 20, 2006; U.S. patent application Ser. No. 11/644,373, entitled Catch members for Occluder Devices, filed on Dec. 22, 2006; U.S. patent application Ser. No. 11/729,045, entitled Screw Catch Mechanism for PFO Occluder and Method of Use, filed on Mar. 28, 2007; U.S. patent application Ser. No. 11/729,636, entitled Adjustable Length Patent Foramen Ovale (PFO) Occluder and Catch System, filed Mar. 29, 2007; U.S. patent application Ser. No. 11/728,906, entitled Catch System with Locking Cap for Patent Foramen Ovale (PFO) Occluder, filed on Mar. 28, 2007; U.S. patent application Ser. No. 11/729, 637, entitled Deformable Flap Catch mechanism for Occluder Device, filed on Mar. 29, 2007; all of which has the same assignee as this application and is incorporated herein in their entirety by reference.

Figure 3A:
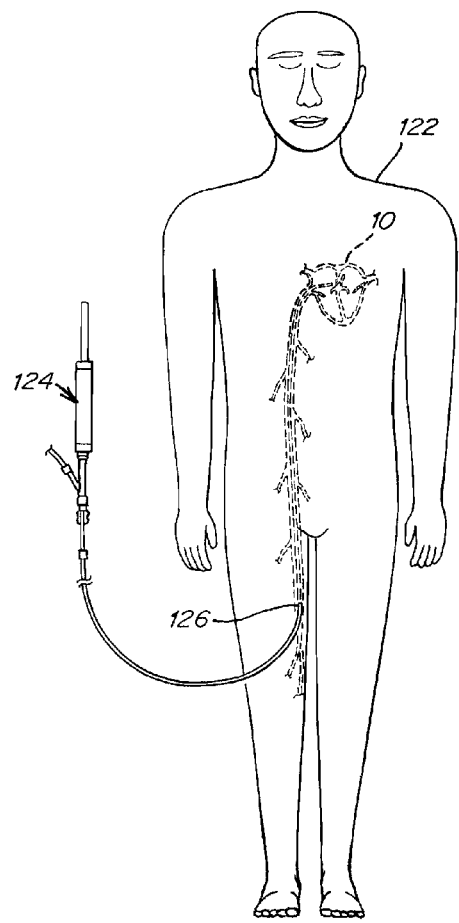
FIG. 3A illustrates insertion of an occluder in a human subject using a delivery system in accordance with an aspect of the disclosure.
Figure 3B:
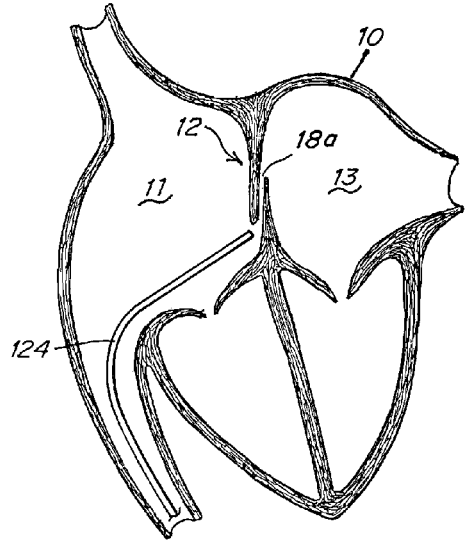
FIG. 3B illustrates introduction of the occluder in a human heart using a delivery system in accordance with an aspect of the disclosure.

FIG. 3A illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 3B.

FIG. 4A illustrates the occluder 70 in the distal end of the delivery assembly 124, which includes a delivery system 140.

A delivery system generally includes a delivery catheter, a delivery wire and a delivery sheath. Because the occluder 70 is delivered percutaneously, the device is secured to the delivery system 140 so that the occluder 70 can be placed accurately at the desired delivery location. Securement systems are provided that attach the occluder to the delivery components. The securement systems are configured to provide accurate delivery of the occluder to the desired delivery location and allow for a controlled deployment so that the position of the device as it is being deployed can be monitored. Also, a device deployed according to this system is able to be retrieved and repositioned until the final stage of the deployment process. In some circumstances, after the final stage of the deployment process, the device can be retrieved. The manner in which the occluder is secured to the delivery system 140 and the process for deployment and/or retrieval of the occluder 70 are described in detail below.

As illustrated in FIG. 4A, the delivery system 140 includes a delivery sheath 144 and a delivery catheter 148. A delivery string or wire 150 extends the length of the delivery assembly to the distal end of the occluder 70. The delivery system 140 constrains the occluder 70 in its elongated delivery configuration. As shown in FIG. 4B, a delivery sheath 144 containing the occluder 70 is first inserted into the right atrium 11 of the patient's heart.

Figure 4C:
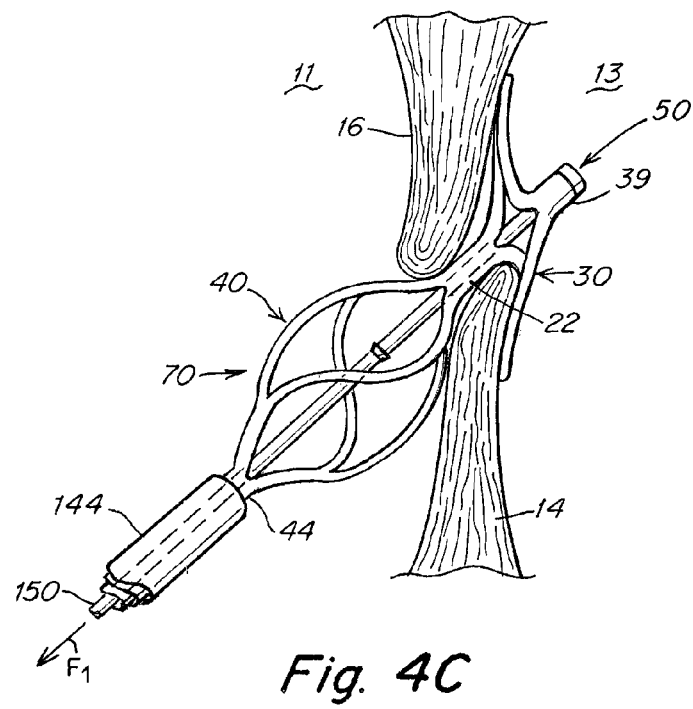

The delivery system, including the delivery sheath 144, may next be inserted through aperture 18 located in the septum 12 (which, in this example, is a PFO tunnel) and into the left atrium 13. Distal side 30 of occluder 70 is then exposed into the left atrium 13 by withdrawing the delivery sheath 144 then pulling force F1 is applied to delivery string or wire 150 such that, for example, a proximal end of the catch element 50 passes through the central tube 22, thereby securing distal side 30 into its deployed state. Delivery sheath 144 is withdrawn further through the aperture 18 and into the right atrium 11, such that central tube 22 is positioned through the aperture 18. As shown in FIG. 4C, proximal side 40 of occluder 70 is then exposed into the right atrium 11, and a relative force between the proximal end 44 of the occluder 70 and the delivery string or wire 150 is applied such that a proximal end of the catch element 50 passes through the proximal end 44 of the occluder 70, thereby securing the proximal side 40 of the occluder into its deployed state. Of course, the occluder 70 should remain in position during deployment of each side of the occluder 70 and pulling forces on the septum tissue should be avoided.

Figure 4D:
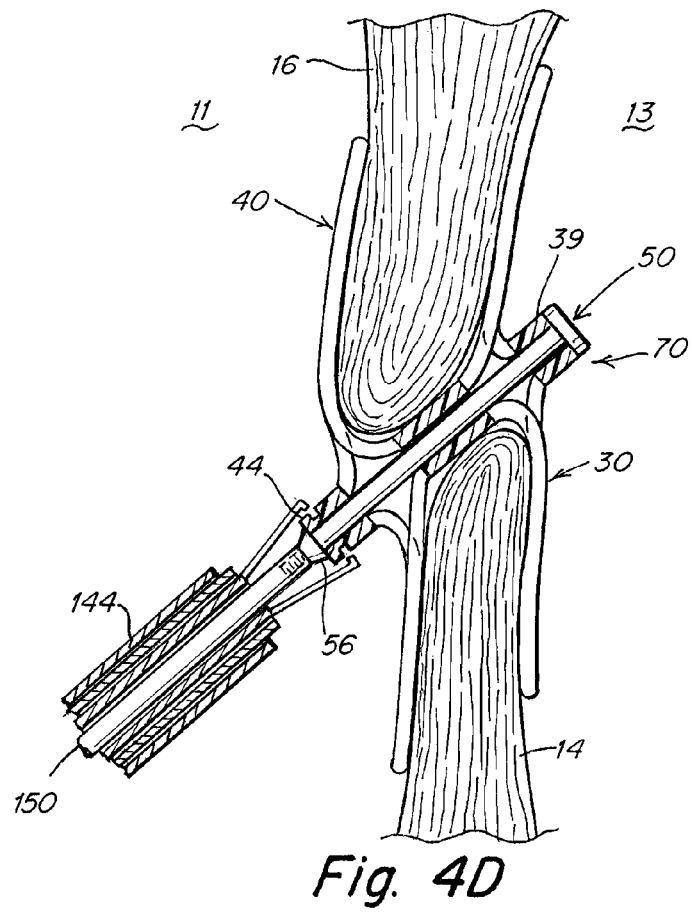

As shown in FIG. 4D, when properly deployed, occluder 70 is disposed through the aperture 18 with a portion of the device on the proximal side and another portion of the device on the distal side. The distal side 30 and proximal side 40 exert a compressive force against septum primum 14 and septum secundum 16 in the left 13 and right 11 atria, respectively, to close the aperture 18, e.g. the PFO. When the occluder 70 is properly located, the securement systems are detached releasing the occluder from the delivery system. This delivery system is then removed from the heart. In the event occluder 70 is not properly deployed after performing the delivery sequence, the occluder 70 may be recovered by reversing the steps of the delivery sequence.

As mentioned above, during the deployment of the occluder 70 in the delivery system 140 described in connection with FIGS. 4A-4D, the occluder 70 is secured to the delivery system 140 at two locations on the occluder 70 so that the occluder 70 can be formed (i.e., compressed) into its deployed configuration. In a preferred form, there are two securements to the delivery assembly 140. A first securement controls the movement of the distal end of the occluder 70 whereby the delivery string or wire 150 holds the catch element and the distal end of the occluder 70 is connected to the distal end of the catch element. The second securement controls the movement of the proximal end 44 of the occlude 70 whereby the occluder 70 is held by the delivery catheter 148. The first and second securements allow the proximal and distal ends of the occluder 70 to be forced together so that the occluder 70 can move from the delivery configuration to the deployed configuration. They also allow the occluder 70 to be forced back into its low profile delivery configuration for redeployment or retrieval. Even if the occluder 70 were constructed from shape memory material (e.g., Nitinol), the occluder 70 would preferably be secured to the delivery assembly 140 by first and second securements.

Both securement systems are able to move relative to one another during the delivery process and as a result, both securement systems cause the occluder 70 to move into the deployed configuration. In the process of delivering the occluder 70, the second securement system is typically released and the first securement system is held while the position of the occluder 70 is evaluated by, for example, fluoroscopy, and if the position of the occluder 70 is appropriate, the first securement system is then released.

FIG. 5 shows delivery assembly 200, which includes a delivery system 220 with an occluder 224 to be delivered. The attached occluder 224 is shown in a deployed configuration for convenience only. Prior to deployment, the occluder 224 would normally be in a low-profile configuration, contained within a delivery sheath 242. FIG. 6 shows delivery assembly 200 in an exploded cross-sectional side view. For convenience, the illustrations have been divided into two parts comprising a control portion 230 of the delivery system 220, and a catheter portion 250 of the delivery system 220 with the attached occluder 224, with the connection indicated by broken line L1. The control portion 230 extends from a delivery wire control rod 232 to a delivery sheath control 240. The catheter portion 250 extends from the delivery sheath control 240 to the end of the delivery system 220 where the occluder 224 is attached. The control portion 230 remains external to the patient and incorporates the features provided for operation of the catheter portion 250 of the delivery system 220. FIG. 7 shows an enlarged cross-sectional side view of the control portion 230. FIG. 8 shows an enlarged cross-sectional side view of the catheter portion 250 and the occluder 224. The basic components of the delivery system 220 are described below by reference to FIGS. 5-8 collectively.

For convenience in describing the function of the controls, the catheter portion 250 is discussed first. Now, referring to FIG. 6, in the catheter portion 250, a delivery sheath 242 encloses the components that are used to deliver occluder 224. A delivery catheter 244 contains an inner delivery wire 246. Both of the delivery catheter 244 and delivery wire 246 connect to the occluder 224 during delivery. Although it may be considered advantageous to eliminate the central lumen in certain embodiments, in other embodiments the delivery wire 246 could also be tubular. The delivery wire 246 should have sufficient tensile and compressive stiffness to withstand the steps required for the deployment and retrieval sequence. In this embodiment, the delivery wire 246 has a stiffer proximal portion and a more flexible distal portion. The delivery catheter 244 also has a stiffer proximal portion and a more flexible distal portion. The combination of stiffness and flexibility facilitates delivery and positioning of the occluder 224. Both the delivery catheter 244 and the delivery wire 246 may be made of two lengths of two different materials joined together in order to provide the requisite degree of stiffness in each portion of the element. Alternatively, the variation of stiffness can be the result of annealing, or some other material treatment process. The more flexible distal portion prevents undue distortion of the septum during the delivery sequence. The delivery wire is further described infra.

Still referring to FIG. 6, the control portion of the delivery system 230 includes respective controls for the delivery sheath 242, the delivery catheter 244 and the delivery wire 246. The delivery wire 246 can be advanced and retracted linearly, in the direction indicated by arrow D', and rotated with respect to the linear axis of the delivery system 220, in the direction indicated by arrow C'. The delivery wire control rod 232 is a rod-like element that provides both linear and rotational control for the delivery wire 246. The delivery wire control rod 232 slides linearly in the direction indicated by arrow C and rotates, with respect to the linear axis of the delivery system 220, in the direction indicated by arrow D to provide the corresponding motion in the delivery wire 246. The delivery catheter 244 can be advanced and retracted linearly, in the direction indicated by arrow A', and rotated, with respect to the linear axis of the delivery system 220, in the direction indicated by arrow B'. A delivery catheter control 234 is a tubular element that provides linear control for the delivery catheter 244, by sliding linearly in the direction indicated by arrow A. A delivery catheter rotational control 238 provides rotational control of the delivery catheter 244, by rotating, with respect to the linear axis of the delivery system 220, in the direction indicated by arrow B. The delivery wire control rod 232 connects to the delivery wire 246 inside the delivery catheter control 234. A perfusion port 236 is provided to permit introduction of fluids into the delivery sheath 242. The delivery sheath 242 can also be rotated, with respect to the linear axis of the delivery system 220, in the direction indicated by arrow F' and extended and retracted linearly along the direction indicated by arrow E'. A delivery sheath control 240 provides linear and rotational control of the delivery sheath 242. The delivery sheath control 240 can be rotated, with respect to the linear axis of the delivery system 220, in the direction indicated by arrow F and slided linearly in the direction indicated by arrow E to induce the corresponding motion in the delivery sheath 242. Thus, all three of the delivery sheath 242, delivery catheter 244 and delivery wire 246 can be independently extended and retracted along and rotated around the longitudinal axis of the delivery system 220 relative to each other using the appropriate controls. The controls are preferably designed to ergonomic specifications. Coordinated operation of the delivery sheath 242, delivery catheter 244 and delivery wire 246 allows for delivery (or retrieval) of the occluder 224. Although in the illustrated embodiment, each element of the catheter portion 250 can be manipulated individually and directly by the user of the delivery system 220, in alternate embodiments, the required operations could be partially or completely automated or synchronized.

Since the occluder 224 is delivered percutaneously, the delivery system 220 must be able to be secured so that the occluder 224 can be placed accurately at the desired delivery location and transformed into its deployed configuration. Securement systems are provided that attach the delivery components to the occluder 224. The securement systems are typically released serially after proper placement of the occluder 224 is confirmed. The securement systems are configured to provide accurate delivery of the occluder 224 to the desired delivery location and allow for a controlled deployment. Also, a device deployed according to this mechanism is able to be retrieved and repositioned until the final stage of the deployment process. It is also possible to retrieve the device once it has been fully released.

Referring to FIG. 8, the delivery catheter 244 and delivery wire 246 both contain features of securement systems on their distal ends for connecting to the occluder 224 and a catch system 180. The delivery wire 246 terminates in a threaded portion 258 having a funnel-like profile. The threaded portion 258 screws onto a mated threaded portion 182 provided on the proximal flange 184 of the catch element 188 for the occluder 224. These two threaded portions cooperatively form the first securement system. The delivery catheter 244 terminates in a threaded portion 256 having a funnel-like profile. The threaded portion 256 screws onto a mated threaded portion 226 provided on the frame of occluder 224. These two threaded portions cooperatively form the second securement system. The first securement system in effect secures the distal end of the occluder to the delivery system 220. The second securement system secures the proximal end 44 of the occluder 224 to the delivery system 220. The two-securement systems cooperatively allow the ends of the occluder 224 to be forced together or apart for deployment or retrieval. The funnel-like profile is useful for locating the corresponding threaded portion of the occluder 224 or the catch element 188 for attachment. The funnel provides a channeling or guiding function. The funnel also helps the delivery system 220 attach to the occluder 224 at extreme angles. The specific geometry of the funnel tips can be modified to achieve better alignment with the device. Application of torque in the appropriate direction engages or disengages each securement system by screwing together or unscrewing the respective elements from each other. The terms "distal" and "proximal" generally refer to the disposition of the securement locations while the occluder 224 is in the delivery configuration in a delivery sheath, but the orientation of the securement systems may change during or after the delivery process.

Still referring to FIG. 8, in a presently preferred embodiment, the threaded portions 256 and 258 are both female threaded, while the corresponding threaded portion 182 of the proximal flange 184 and threaded portion 226 are male threaded. This configuration has several advantages. First, a male thread in the occluder eliminates a cavity in the occluder 224 in which blood can stagnate and promote clotting. Second, the profile of the occluder 224 is reduced by using the male thread. Finally, the female connectors on the delivery system 220 can be provided with the funnel-like guides described above. In alternate embodiments, the male threads may be disposed on threaded portions 256 and 258. Also, threaded portions 256 and 258 need not have the same type of threads.

Figure 11:
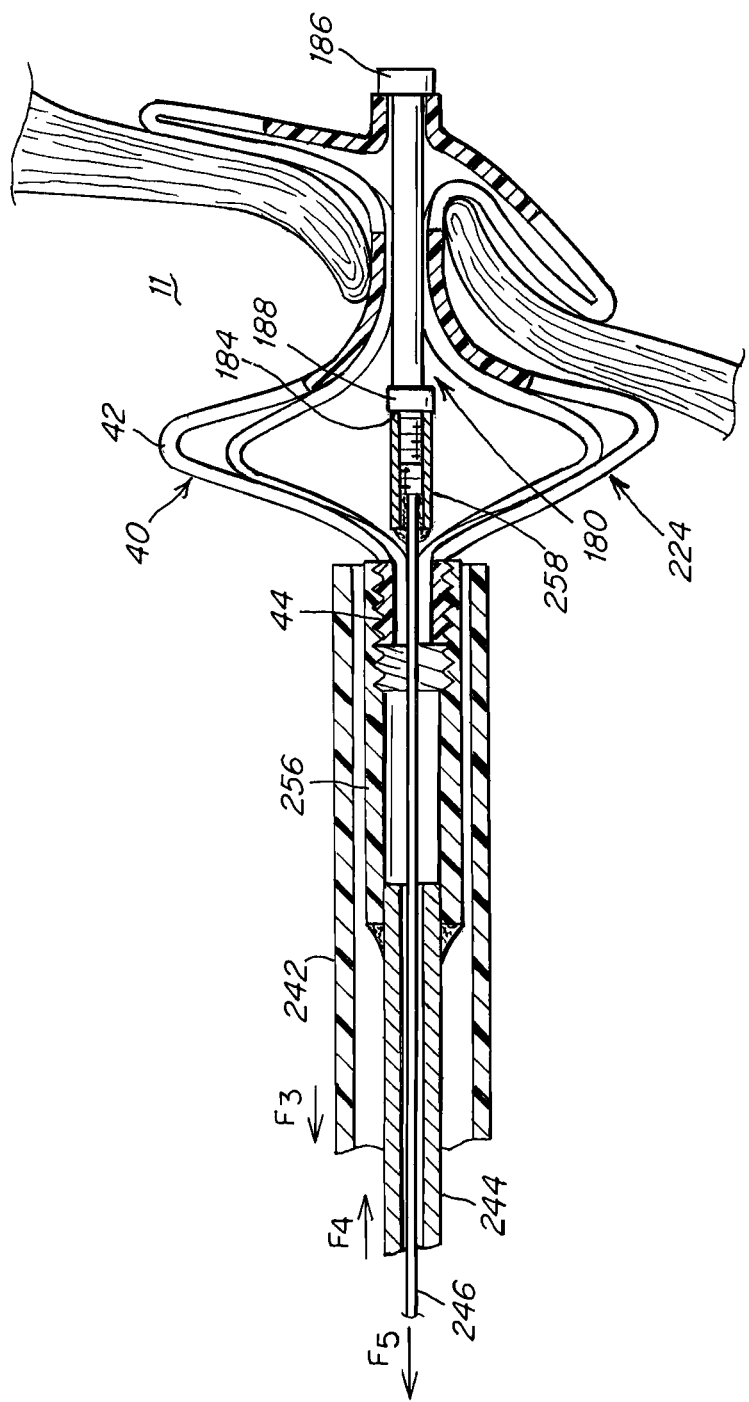
FIG. 11 is a cross-sectional side view of one step in a deployment sequence according to an aspect of the disclosure.

Deployment of the occluder to a desired site is typically a multi-step operation. In FIGS. 5 and 6, the occluder 224 is shown outside the delivery catheter for purposes of illustration. As shown in FIG. 9, the delivery sheath 242 contains occluder 224 in its elongated, delivery form, with the catch element 188 disengaged. As discussed above with reference to FIGS. 3A and 3B, the distal end of the delivery sheath 242 with the enclosed occluder 224 is first inserted into the right atrium 11 of the patient's heart. The distal end of the delivery sheath 242 with the enclosed occluder 224 may next be inserted through the anatomical aperture 18a located in the septum 12, and into the left atrium 13. The distal side 30 of occluder 224 is then deployed into the left atrium 13. The deployment process is described further below. As shown in FIG. 10, the delivery sheath 242 is withdrawn through the anatomical aperture 18a into the right atrium 11, such that central tube 22 of the occluder 224 is positioned through the anatomical aperture 18a. As shown in FIG. 11, the proximal side 40 of the occluder 224 is then deployed into the right atrium 11. When properly deployed, the central tube 22 is disposed at the anatomical aperture 18a, and the distal side 30 and proximal side 40 exert a compressive force against septum primum 14 in the left atrium 13 and septum secundum 16 in the right atrium 11, respectively, to close the anatomical aperture 18a, e.g. the PFO. When the occluder 224 is properly deployed, the delivery system 220 is detached from the occluder 224, and the delivery sheath 242 with the delivery catheter 244 and delivery wire 246 are then withdrawn from the heart. In the event that the occluder 224 is not properly deployed after performing the procedure described above, the occluder 224 may be recovered by reversing the steps of the delivery sequence. These sequences are described in more detail below.

FIG. 9 illustrates the initial step for a typical delivery sequence in accordance with one aspect of the disclosure, a high level view of which is shown in FIG. 3B. The occluder 224 and catch system 180 are secured to the delivery wire 246 and to the delivery catheter 244, respectively. The female threaded portion 256 of the delivery catheter 244 is screwed onto the male threaded portion 226 of the occluder 224. The female threaded portion 258 of the delivery wire 246 is screwed onto the male threaded portion 182 of the catch element 188 of the occluder 224. The distal end of the delivery sheath 242 with the enclosed occluder 224 is inserted through the aperture to be occluded, such as the anatomical aperture 18a of FIG. 1, to approximately the midpoint of the occluder 224.

Referring now to FIG. 10, the distal side 30 of the occluder 224 is deployed on the distal side of the aperture in the left atrium 13. The distal portion 30 is deployed by first retracting the delivery sheath 242 to expose the distal portion 30 of the occluder 224. The axial length of the occluder 224 is then reduced by applying pulling force F1 on delivery wire 246 with sufficient force to cause the catch element 188 to be pulled through the central tube 22 of the occluder 224 and the distal portion 30 of the occluder 224 to compress and distal petals 32 to form. Force F2 is simultaneously applied to the delivery catheter 244 to hold the occluder 224 stationary. The central tube 22 of the occluder 224 catches on the catch element 188. This holds the distal petals 32 in place while the remainder of the deployment sequence is carried out.

Figure 12:
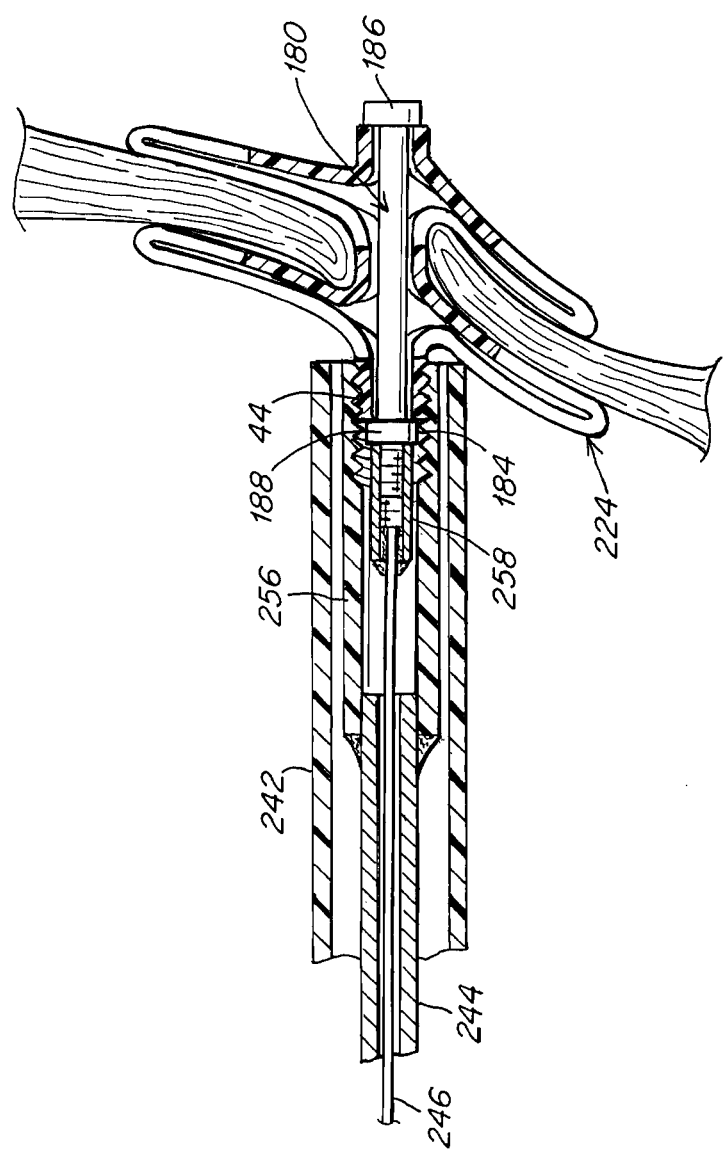
FIG. 12 is a cross-sectional side view of one step in a deployment sequence according to an aspect of the disclosure.

Referring now to FIG. 11, the proximal side 40 of the occluder 224 is deployed on the proximal side of the aperture in the right atrium 11. The proximal portion 40 is deployed by first retracting the delivery sheath 242 to expose the proximal portion 40 of the occluder 224. The proximal petals 42 are then deployed by simultaneously advancing the delivery catheter 244 by applying force F4 and retracting the delivery wire 246 by applying force F5 to maintain the position of the occluder 224. Eventually, the proximal end 44 of the occluder 224 is pushed over the proximal end 44 of the catch element 188 and the occluder 224 is caught on the proximal flange 184 of the catch element 188. The final configuration is illustrated in FIG. 12. The occluder 224 can now be evaluated for proper deployment at the desired location.

Figure 13:
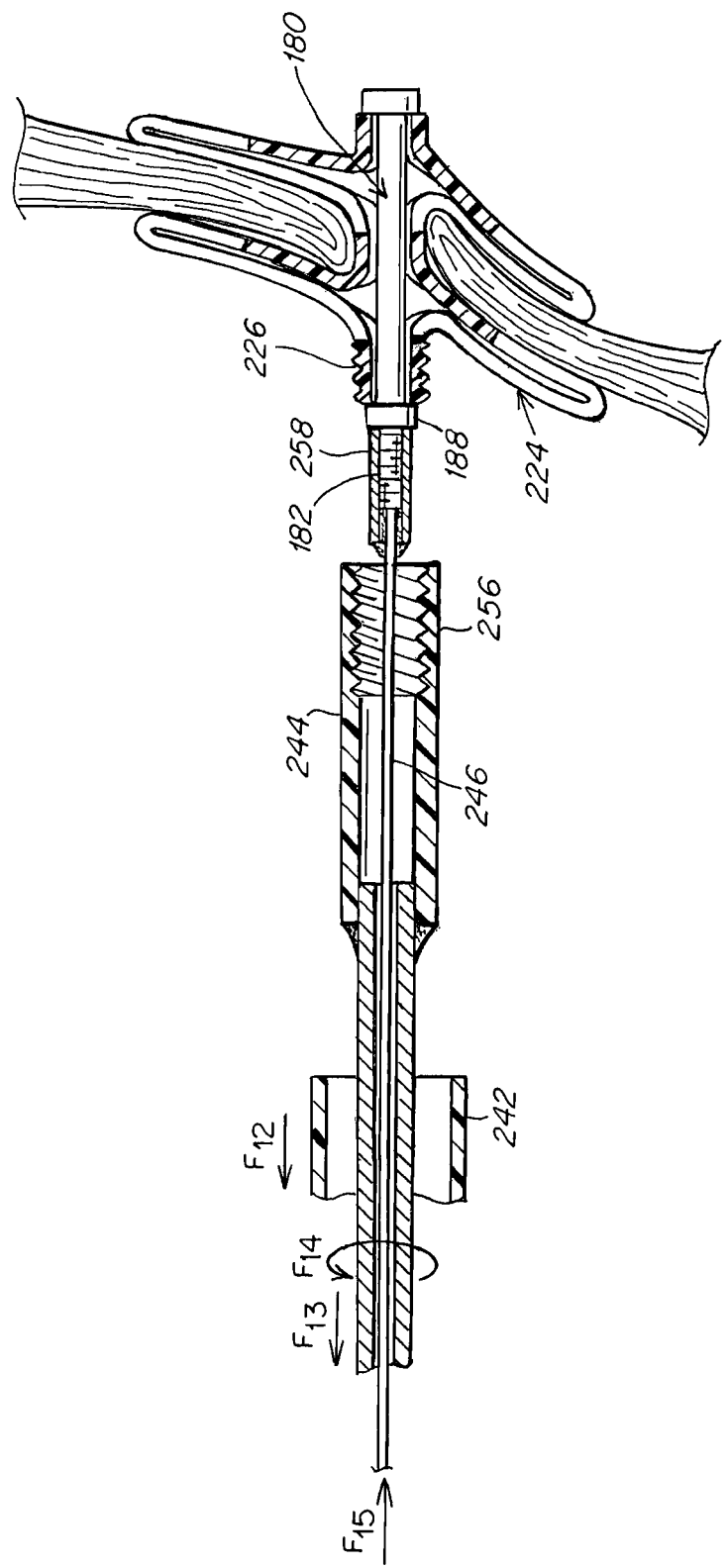
FIG. 13 is a cross-sectional side view of one step in a detachment sequence according to an aspect of the disclosure.
Figure 14:
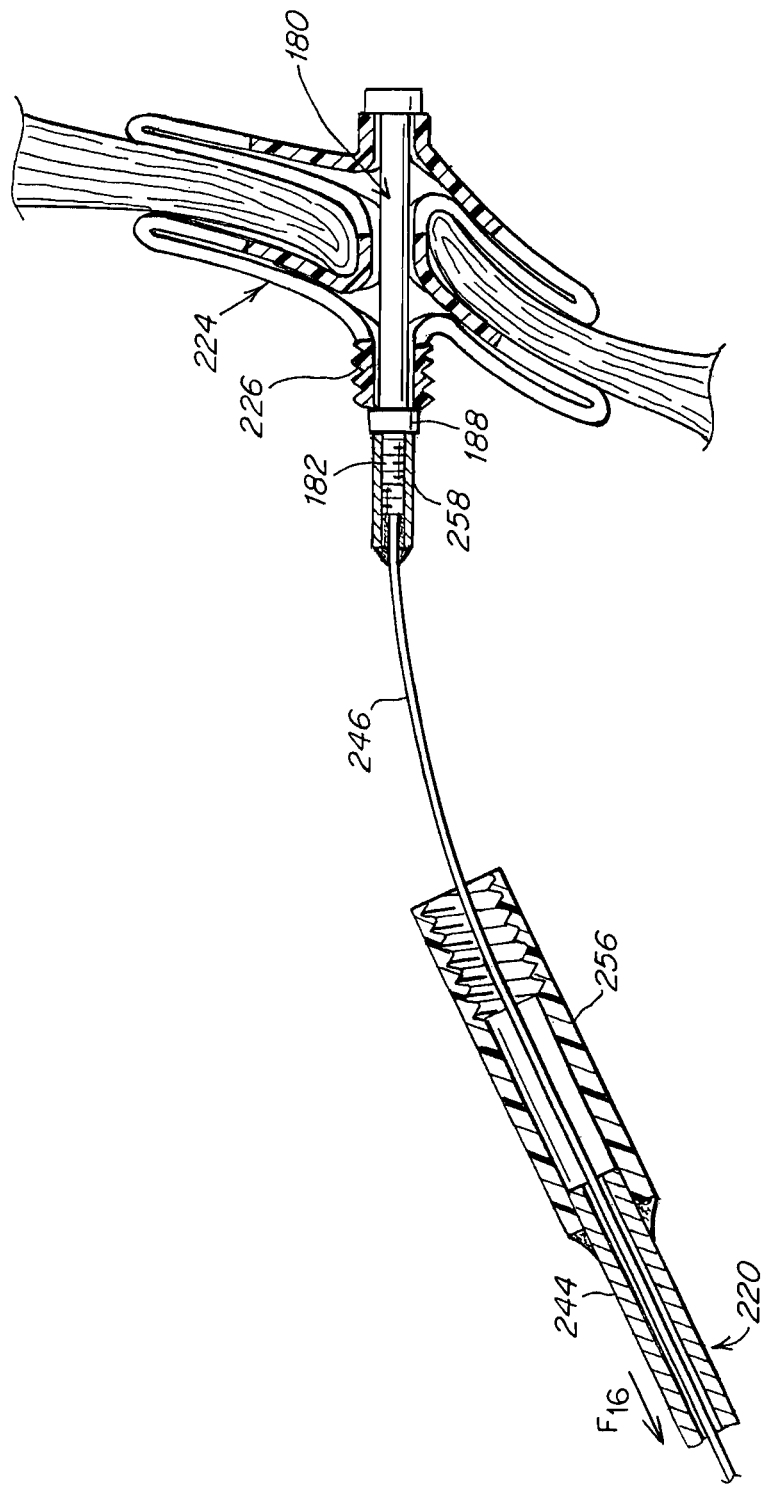
FIG. 14 is a cross-sectional side view of one step in a detachment sequence according to an aspect of the disclosure.

The occluder 224 can be evaluated for proper deployment with the delivery system 220 attached or at least partially detached. The delivery system 220 can be partially detached by releasing one of the securement systems provided by the delivery catheter 244 and the delivery wire 246. As shown in FIG. 13, according to one preferred embodiment, to evaluate the proper deployment of the occluder, if desired, the delivery sheath 242 can be further retracted and the delivery catheter 244 can be detached from the occluder 224. The delivery catheter 244 can be detached by applying torque to unscrew the delivery catheter 244 from the proximal threaded portion 226 of the occluder 224 and retracting the delivery catheter 244. The delivery wire 246 continues to secure the occluder 224, as illustrated in FIG. 14. This affords the clinician a substantially unobstructed view of the occluder delivery site in order to evaluate the placement of the occluder 224. In addition, the more flexible distal portions of the delivery catheter 244 and the delivery wire 246 allow the distal end of the delivery system 220 and the deployed occluder to be re-positioned so that the view is not obstructed. The positioning of the occluder 224 can be evaluated using fluoroscopy or other appropriate techniques. If the delivery or deployment is not satisfactory, then the delivery system 220 can be used to retrieve the occluder 224. If delivery catheter 244 has been detached, it is reattached by advancing the threaded portion 256 of the delivery catheter 244 toward the threaded portion 226 of the occluder 224 and applying torque until the delivery catheter 244 is threaded onto the occluder 224. As mentioned before, the funnel-like shape of the threaded portion 256 of the delivery catheter 244 helps to guide the reattachment of this securement system. A similar technique is used to reattach the delivery wire 246 if needed.

Figure 15:
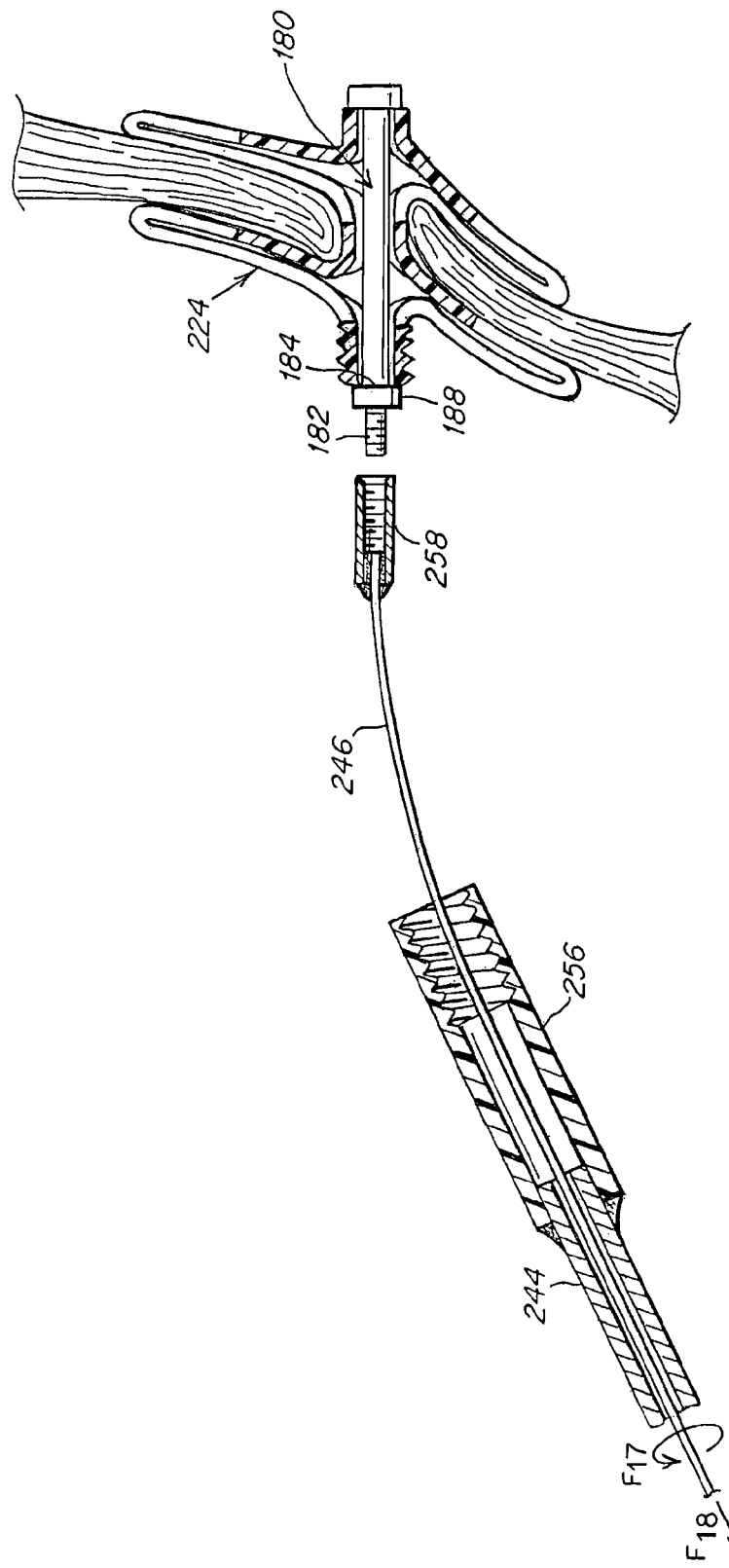
FIG. 15 is a cross-sectional side view of one step in a detachment sequence according to an aspect of the disclosure.

Once the occluder 224 is successfully deployed, the delivery system 220 can be detached in the sequence shown in FIGS. 13-15. As illustrated in FIG. 13, the delivery sheath 242 is partially retracted by applying force F12. Also, the delivery catheter 244 is detached by applying torque F14 to unscrew the threaded portion 256 of the delivery catheter 244 from the threaded portion 226 of the occluder 224. Force F13 is then applied to retract the delivery catheter 244 while simultaneously advancing the delivery wire 246 by applying force F15 to maintain the position of the occluder 224. The occluder 224 remains attached to the delivery system 220 by the second securement system provided by the delivery wire 246. As discussed above, if retrieval is desired for any reason, the occluder 224 can readily be returned to its low-profile configuration and removed at this point. As shown in FIG. 14, the delivery catheter 244 can be further retracted by applying force F16 to provide an unobstructed view of occluder 224, again while the delivery wire 246 remains attached. As illustrated in FIG. 15, if the deployment is successful, then the delivery wire 246 can be detached by applying torque F17 to unscrew the threaded portion 258 of the delivery wire 246 from the threaded portion 182 of the catch element 188. The torque applied to remove the delivery wire 246 and the delivery catheter 244 can be either clockwise or counterclockwise depending on the design of the device. The delivery wire 246 can be retracted by applying force F18. The occluder 224 is now fully deployed.

Figure 16:
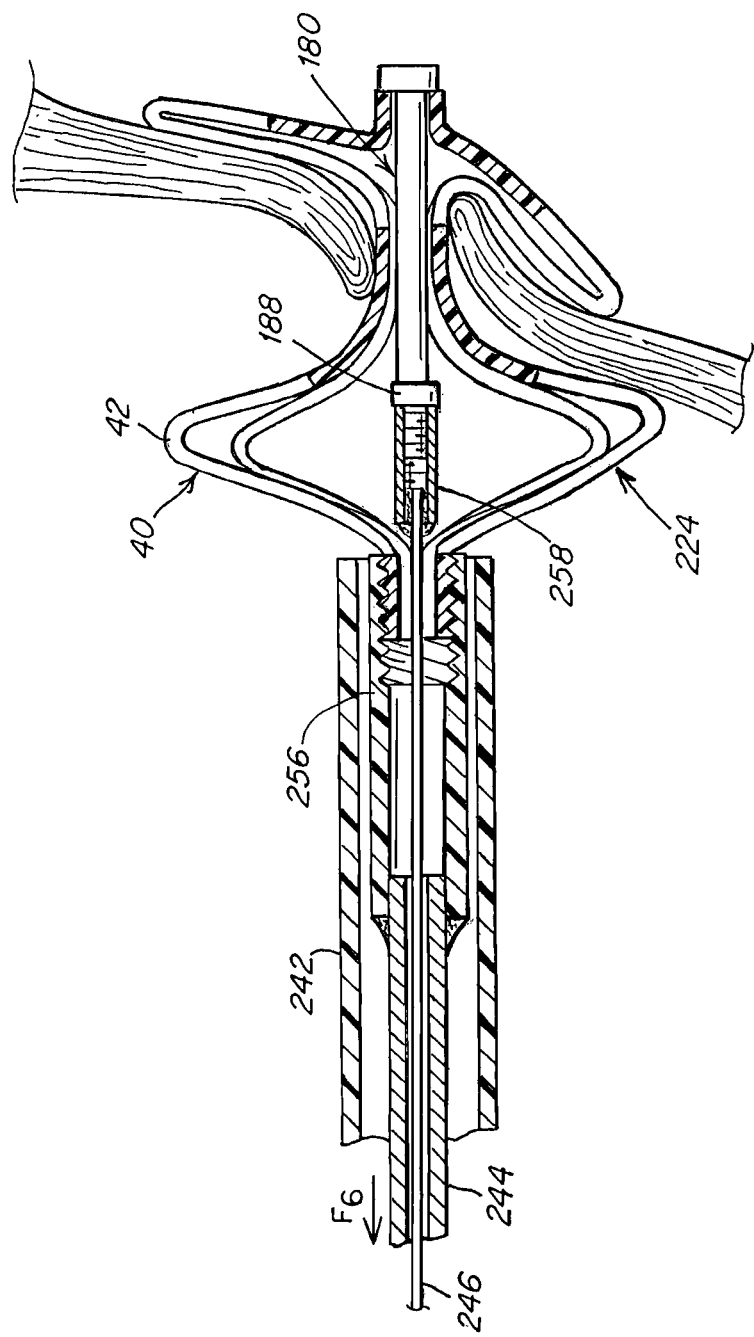
FIG. 16 is a cross-sectional side view of one step in a retrieval sequence according to an aspect of the disclosure.
Figure 17:
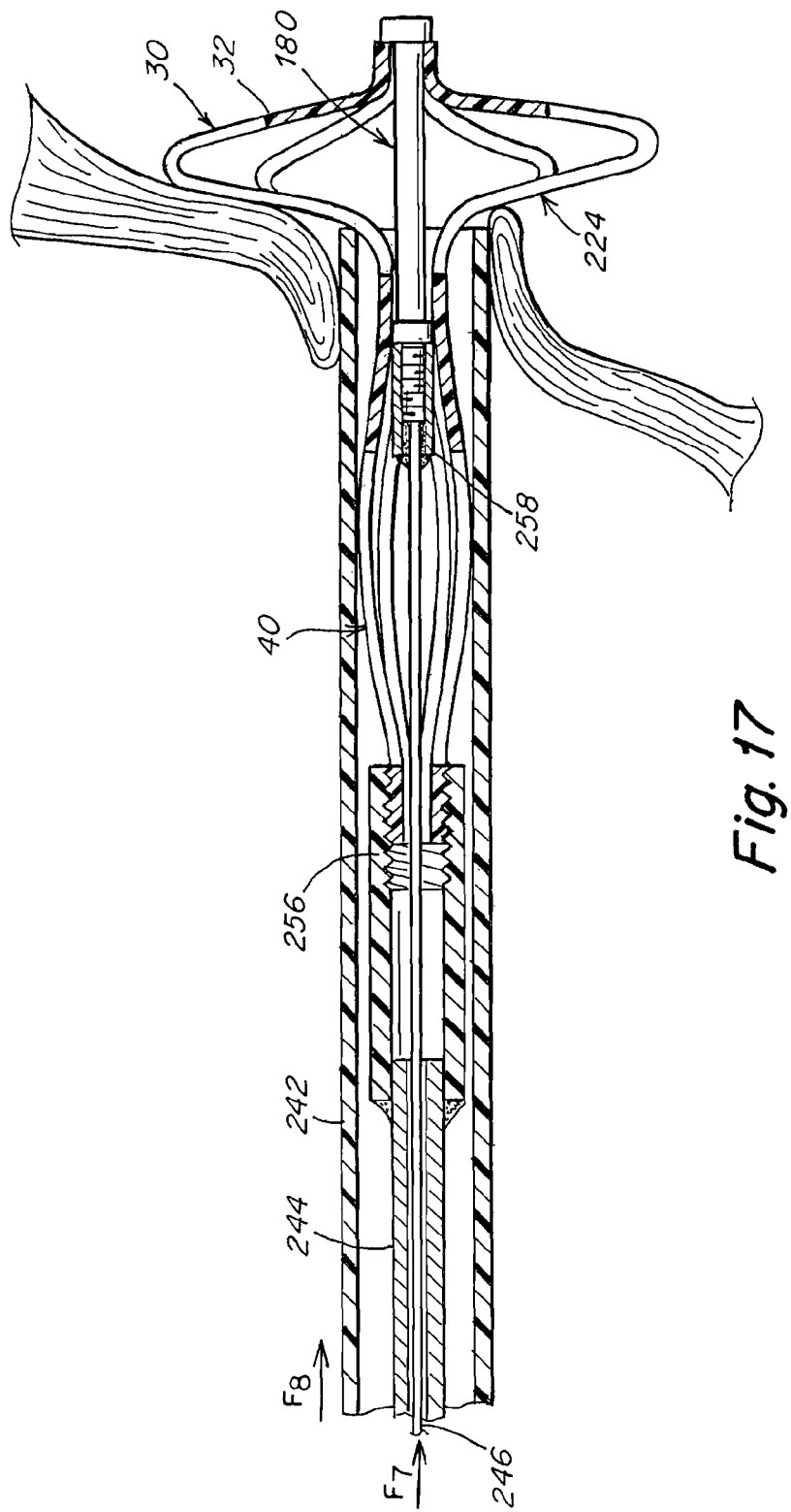
FIG. 17 is a cross-sectional side view of one step in a retrieval sequence according to an aspect of the disclosure.
Figure 18:
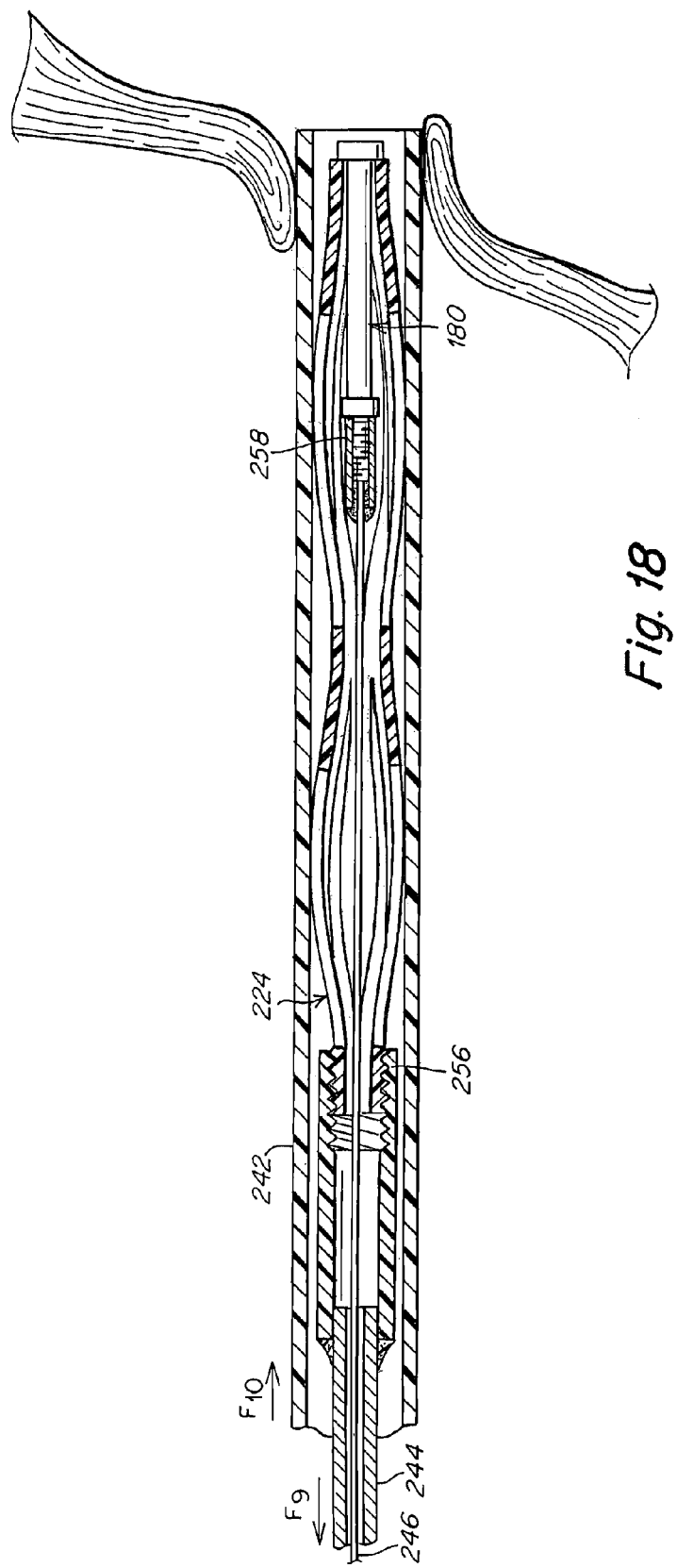
FIG. 18 is a cross-sectional side view of one step in a retrieval sequence according to an aspect of the disclosure.
Figure 19:
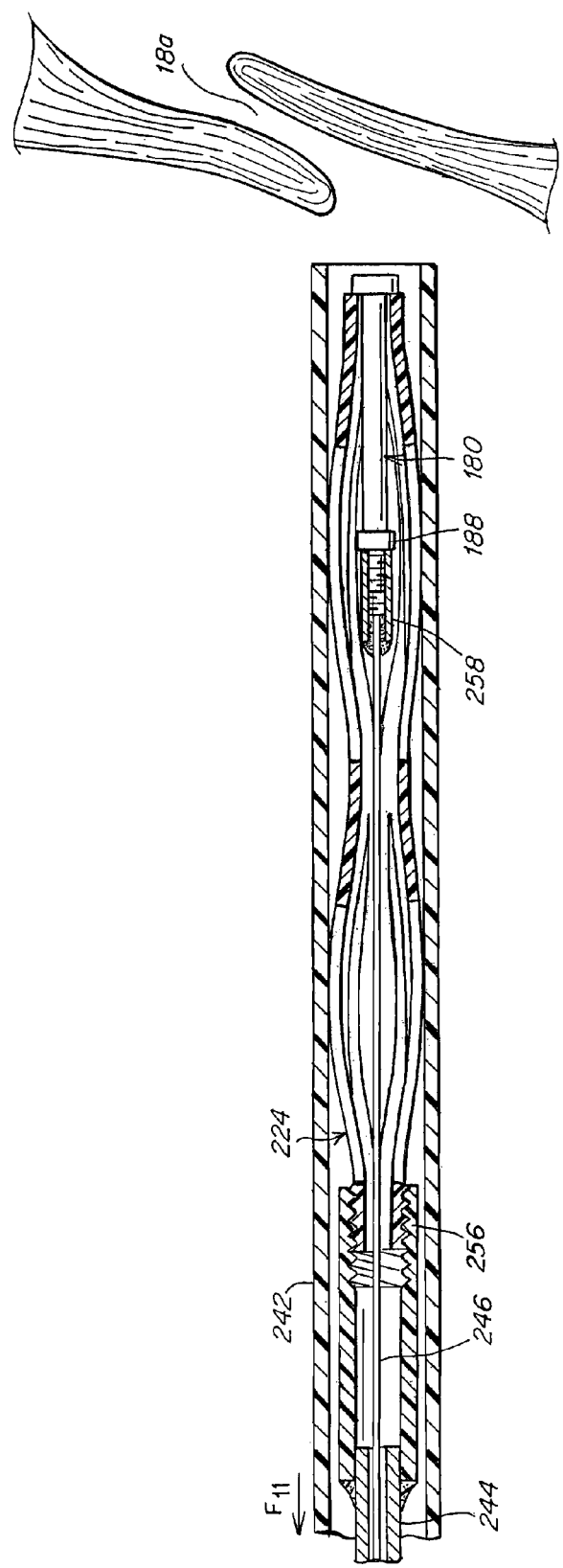
FIG. 19 is a cross-sectional side view of one step in a retrieval sequence according to an aspect of the disclosure.

Referring now to FIG. 16, if retrieval is desired, the process involves reattaching the delivery catheter 244 and delivery wire 246 as mentioned above. Then force F6 is applied to the delivery catheter 244 to pull the proximal portion 40 of the occluder 224 over the proximal end of the catch element 188. As the axial length of the occluder 224 is increased, the proximal petals 42 are unformed and the proximal portion 40 of the occluder 224 returns to its tubular profile. Referring to FIG. 17, force F8 is applied to the delivery sheath 242 to advance the delivery sheath 242 over the proximal portion 40 of the occluder 224 and retain the proximal portion 40 of the occluder 224 in the low-profile configuration. Also, force F7 is applied to delivery wire 246 in order to release the distal portion 30 of the occluder 224 and further increase the axial length of the occluder 224. Referring now to FIG. 18, the distal portion 30 of the occluder 224 is fully extended back into it low-profile configuration and forces F9 and F10 are applied to the delivery sheath 242 and the delivery catheter 244 in order to retrieve the occluder 224 back into delivery sheath 242. Referring to FIG. 19, the delivery sheath 242 and enclosed occluder 224 are removed from the anatomical aperture 18a and can further be fully removed from the heart 10 by applying force F11. This step can also be used as a starting point for redeployment of the occluder 224, i.e., the sequence shown beginning in FIG. 9.

Figure 20:
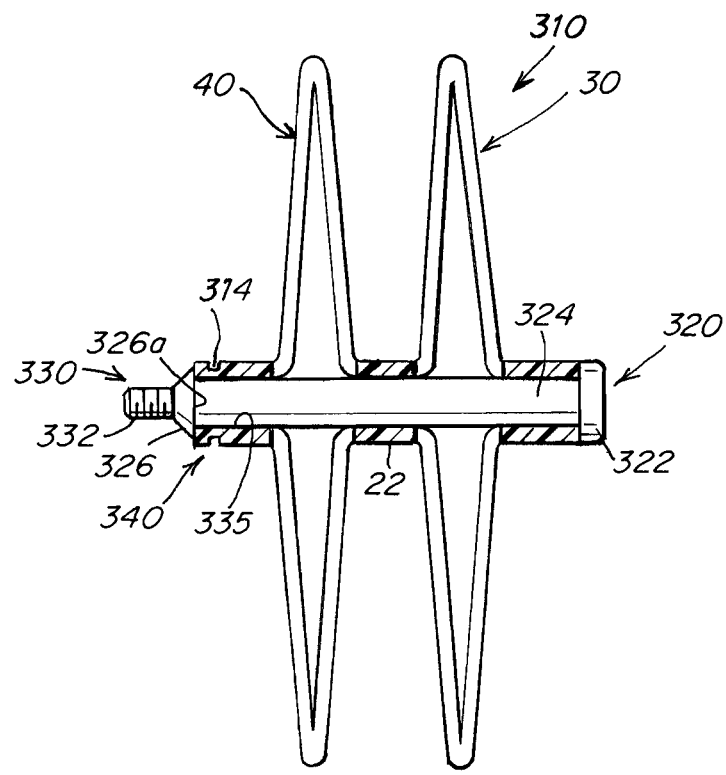
FIG. 20 illustrates a cross-sectional schematic of a deployed occluder according to an aspect of the disclosure.

The components of an alternate preferred embodiment of the invention are described in connection with FIGS. 20-24. FIG. 20 illustrates an occluder 310 with a distal side 30 and a proximal side 40 that are connected by central tube 22. The configuration illustrated is a simplified schematic view of the occluder illustrated in FIGS. 2A-2D. Of course, other types of occluders can be deployed using this delivery system. The occluder includes a catch system 320 that includes a distal flange 322, a catch body 324 and a catch element 326 in the shape of a cone. The catch system 320 is disposed in an axially central location in the occluder 310. Although schematically illustrated as a separate piece than the proximal side and distal side loops 40 and 30, respectively, of the occluder, the catch system 320 may be a single piece, or even fixed to one end of the tube that forms the proximal and distal loops by an adhesive, ultrasonic welding, or the like. For example, the flange 322 may be fixed to the end of the tube that forms the loops. The device can be formed from a single component or multiple components that are fixed together. The catch body 324 is disposed axially within the inside surface of the tube that forms the loops. The tube is able to move with respect to the catch system (and the catch body) so that the petals can move from the delivery configuration to the deployed configuration. The inside surface of the tube 335 is able to slide over the catch element 326 so that, when the proximal tip of the occluder 310 rests against the flat surface 326a of the catch element 326, the occluder 310 is secured in its deployed configuration.

Figure 21:
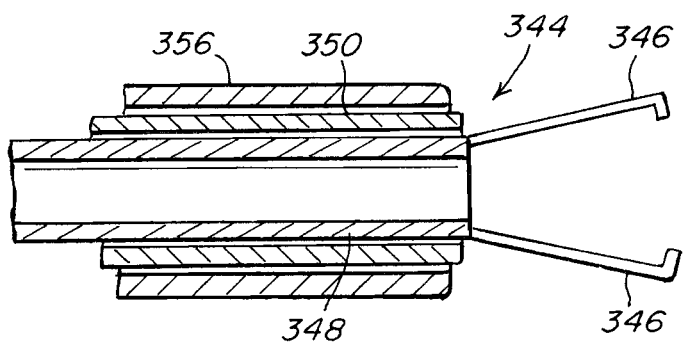
FIG. 21 illustrates a cross-sectional side view of several components of the delivery system according to one embodiment of disclosure.

As shown in FIG. 20, the first securement system 330 includes a threaded component 332, illustrated as a male thread, and corresponding threads on a corresponding female portion described below in connection with FIGS. 22 and 23. The second securement system 340 includes a groove 314 on the proximal portion 40 of the occluder 310 that cooperates with a collet system 344 described below in connection with FIGS. 21 and 22. As shown in FIG. 21, the collet system 344 also includes collet fingers 346 that are configured to have ends that fit within the groove 314 on the occluder 310. The collet system also includes a collet tube 348 onto which the collet fingers 346 are mounted and a collet sheath 350 that is movable with respect to the collet tube 348. In one embodiment, the collet fingers 346 are constructed of nitinol and have a splayed configuration when at rest as illustrated in FIG. 21. More detail regarding the construction of the construction of the collet fingers 346 is provided below. As the end of the collet sheath 350 is moved over the collet fingers 346, the collet fingers 346 are moved radially inward and when occluder 310 is being positioned in the delivery system, the collet fingers 346 are moved radially inward and engage the groove 314 on the occluder 310 (illustrated on the left side of FIG. 22). The collet sheath 350, collet tube 348 and collet fingers 346 are described in more detail below.

FIG. 22 illustrates a delivery system of a preferred embodiment of the invention. Specifically, the occluder 310 is disposed within the delivery sheath 356. Within the delivery sheath 356 are the components that are used to secure the occluder 310 during delivery and are (typically) released serially after proper placement of the occluder 310 is confirmed. The first securement system 330 and the second securement system 340 are each illustrated as securing the occluder 310 for delivery to the desired delivery location within the body. The securement systems 330 and 340 are configured to provide accurate delivery of the occluder 310 to the desired delivery location and allow for a controlled deployment so that the position of the device as it is being deployed can be monitored. Also, an occluder 310 deployed according to this system is able to be retrieved and repositioned until the final stage of the deployment process. Even after the final stage of the deployment process, the occluder 310 can be retrieved.

FIG. 22 also illustrates the second securement system 340 in an engaged configuration. Specifically, the collet fingers 346 are disposed in the collet sheath 350 so that the collet fingers 346 engage groove 314 on the occluder 310. When the collet sheath 350 is disposed in this configuration, the occluder 310 is secured by the collet fingers 346 against axial motion with respect to the collet sheath 350 and collet tube 348. Similarly, when the delivery wire 380 is secured in an engaged configuration, the occluder 310 is secured against axial motion with respect to the delivery wire 380. Thus, the occluder 310 is secured during delivery and the controlled motion of the collet sheath 350/collet tube 348 and the delivery wire 380 can deploy the occluder 310.

As illustrated in FIG. 22, the delivery wire 380 is threaded into the first securement system 330 by a threaded connection. As illustrated in FIG. 22, the female threads can be disposed on the delivery wire 380 and the male threads can be disposed on the catch element 326. FIG. 24 illustrates an alternative embodiment of a first securement system, designated 390, in which the male threaded portion 392 is disposed on the delivery wire 380 and the female threaded portion 394 is disposed on the catch element 326.

In a presently preferred embodiment, the male threads are disposed on the catch element 326 and the female threads are disposed on the delivery wire 380. This configuration has several advantages. First, the catch element 326 does not need a female connector and there is no cavity in which blood can stagnate and promote clotting. Second, the space required for the threaded connector 392 on the catch element 326 is diminished. Finally, a female connector on the delivery wire 380 may allow for a more smooth deployment of the catch element 326.

The first securement system interconnects the delivery wire 380 to the threaded portion on the catch element 326. Representative embodiments of the first securement system and its components are illustrated in more detail in FIGS. 23 and 24. In FIG. 23, the threaded portion 386, interconnects the delivery wire 380 and the threaded portion 332 on catch element 326, illustrated in FIG. 20.

Referring again to FIG. 23, the delivery wire 380 has a more rigid section 382 and a more flexible section 384. In general, the flexible section 384 is distal to the more rigid section and is provided on the delivery end of the delivery wire 380. The delivery wire 380 can be any kind of flexible elongate member such as a wire, tube, hypotube, coil, or other hollow or solid constructions. The delivery wire 380 can be made from any material suitable for medical applications. Exemplary materials include metals and alloys suitable for medical applications, including stainless steel (such as "304 Stainless") and MP35N, polymers (such as nitinol), or any other suitable materials. The variation of stiffness can be the result of annealing; other material treatment process, or it may be a result of different materials being joined together. The amount of flexibility, or rigidity, can vary depending on the type of occluder being delivered and the delivery location within the body. The length of the flexible section 384 would typically be about the length of the occluder 310 in its delivery configuration. That is, the occluder 310 in the delivery configuration would surround the flexible portion of the delivery wire 380. The length of the flexible section 384, however, can be varied. The distal end of the delivery wire 380 includes a threaded attachment portion 386 on the end of the flexible section 384, described in detail below. The threaded portion 386 is illustrated as a female thread.

Figure 25A:
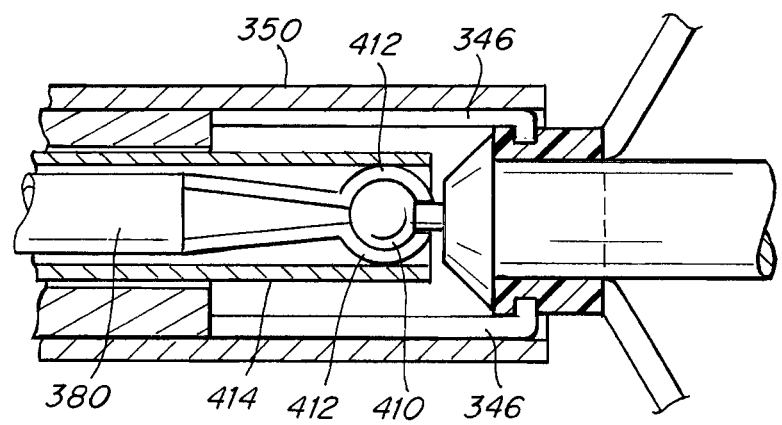
FIGS. 25A, 25B, 26A, 26B, 27A and 27B are alternative configurations for the first securement system according to aspects of the disclosure.
Figure 25B:
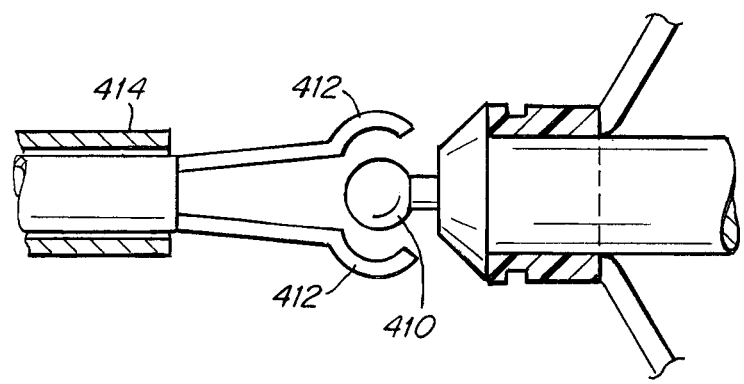

FIGS. 25A, 25B, 26A, 26B, 27A, and 27B illustrate alternative embodiments of the first securement system 330. Generically, all of the securement embodiments described can be properly described as interlocking systems. Each of these embodiments of the first securement system can be used with the threaded or collet connection for the second securement system and provide alternatives which may be appropriate for different kinds of occluding devices or other devices that could be delivered by the delivery system described in this application FIGS. 25A and 25B illustrate a ball and claw type attachment. In place of a screw type attachment, a ball 410 is disposed on the catch element and two or more claws 412 are sized to secure the ball 410 within the claws 412. The claws 412 are disposed at the distal end of the delivery wire 380. Two claws 412 are illustrated in FIG. 25B. The claws 412 operate under a similar principle as the collet design described previously. Specifically, there is a claw sheath 414 that is axially movable with respect to the claws 412. As illustrated in FIG. 25B the claws 412 splay out in the at rest configuration. When the claws 412 are in the claw sheath 414, the claws 412 are sized to secure the ball 410. Thus the configuration in effect allows for a secure placement of the occluder on the delivery system. When the occluder is ready to be released claw sheath 414 is withdrawn and the claws 412 splay out to the at rest configuration. Thus the occluder is released from the first securement system.

Figure 26A:
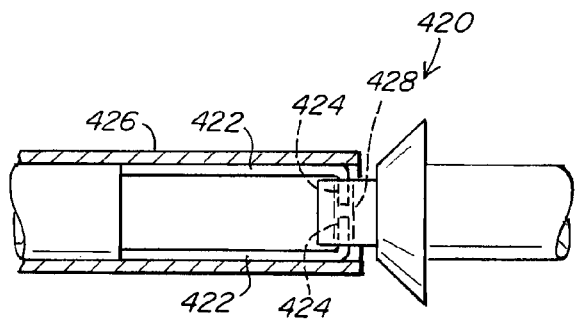
Figure 26B:
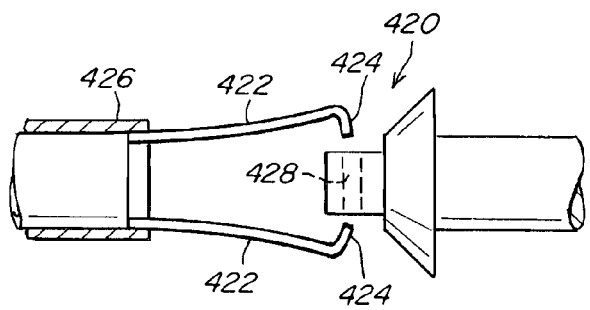

FIGS. 26A and 26B illustrate a pin-through-hole connector 420. In this embodiment, fingers 422 includes pins 424 that are disposed in an aperture in the catch element. As the example illustrates, the transverse aperture 428 is formed in the catch element and the transverse aperture 428 is sized to receive the pins 424. When the fingers 422 including pins 424 are in a sheath 426, the pins 424 are secured within the transverse aperture 428. Thus the configuration in effect allows for a secure placement of the occluder on the delivery system. When the occluder is ready to be released a sheath 426 is withdrawn and the pins 424 spring back to the unbiased position similar to the fingers in the collet system. Thus the occluder is released from the first securement system.

Figure 27A:
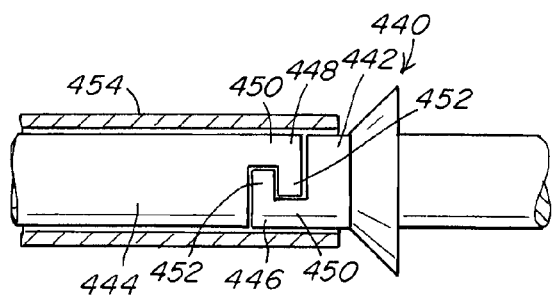
Figure 27B:
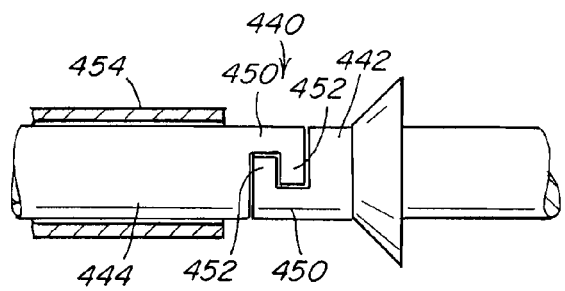

In another embodiment of the first securement system, illustrated in FIGS. 27A and 27B, a pair of cooperating configurations are secured when disposed within a sheath and separable when the sheath is withdrawn. This is a type of interlocking system 440. In this example, the lock is achieved using a combination of two C-shaped elements. Specifically, as illustrated, the catch element has a portion 442 that extends in an axial direction and is adapted to mate with a delivery wire 444. The portion 442 and the delivery wire 444 have cooperating extensions 446, 448 respectively that are able to interlock as illustrated in FIG. 27A. The system as illustrated has an interlocking elbow/arm attachment 450, 452 on each of the protrusion and the delivery wire. A variety of interlocking configurations are possible and the concept should not be limited to the configuration illustrated. When the interlocking system is disposed within a sheath 454, the cooperating extension cannot move with respect to each other. Thus the configuration in effect allows for a secure placement of the occluder on the delivery system. When the cooperating extensions are extended beyond the sheath 454, the interlocking system can release and the occluder is released from the first securement system.

Figure 28:
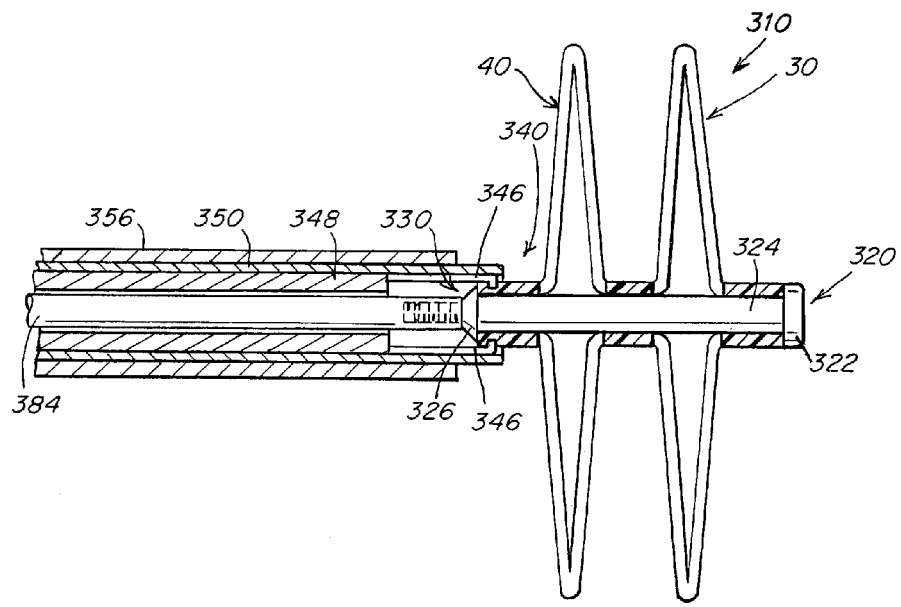
FIGS. 28 and 29 are detail cross-sectional side view of the delivery system during two steps in the deployment process according to one aspect of the disclosure.
Figure 29:
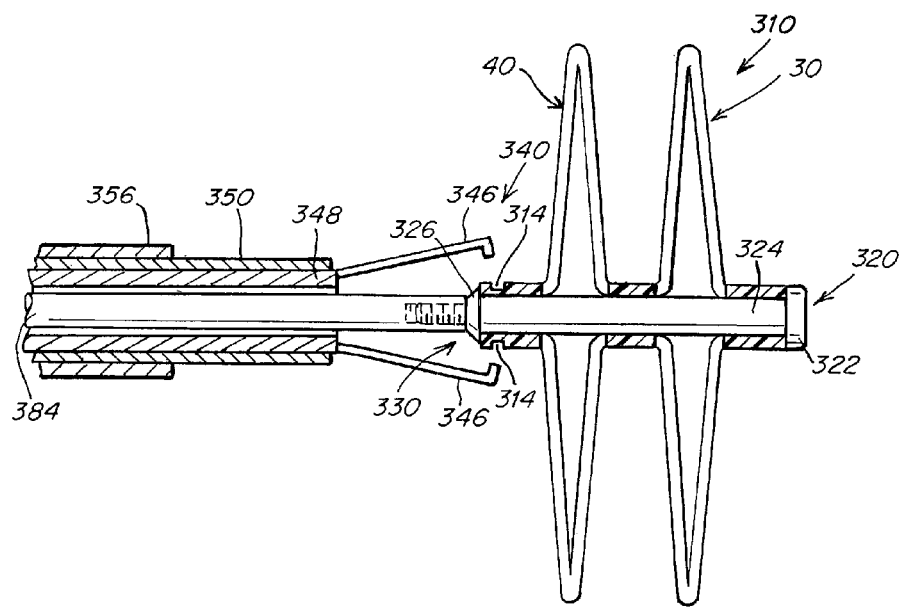

Any of the previous embodiments described in FIGS. 20-27B can be deployed in a manned illustrated in FIGS. 28 and 29. FIG. 28 illustrates the occluder 310 in its deployed configuration. To deploy the occluder 310, the delivery sheath 356 is withdrawn to expose the distal side loops 30 and then the proximal side loops 40 into the defect to be occluded. During this time the catch element 326 is engaged so that the occluder 310 is secured in the deployed configuration. Once the occluder 310 is in the deployed configuration the collet sheath 350 is withdrawn and the collet fingers 346 are unconstrained by the collet sheath 350 and are allowed to move radially outward to the unbiased condition, as illustrated in FIG. 29. Once the collet fingers 346 move radially outward the tips of the collet fingers 346 move away from the groove 314 in the occluder 310. Accordingly, the occluder 310 is only attached to the delivery by the first securement system 330. In this position, the clinician is able to evaluate the position of the occluder 310 to make sure that the device is properly positioned.

The process of retrieving an occluder varies based on the state of the delivery when the decision to retrieve the occluder is made. If the second and first securement systems are still attached and the catch system has not secured the device in the deployed configuration, then the retrieval process is simply a reversal of the deployment process. The second securement system is pulled and the device can be withdrawn into delivery sheath 356 and removed from the body.

If the catch system has secured the device in a deployed configuration, and the second and first securement systems are still attached, the process is the same with the addition of moving the catch element of the occluder relative to the second securement so that the device can be elongated. Once that occurs, the device can be withdrawn as described above.

The retrieval process for an occluder in which the second securement system is a collet system, which has been disengaged, requires an additional step. The collet system is advanced until the collet fingers are in alignment with the groove on the occluder. Next the collet sheath is advanced over the collet fingers such that the fingertips fit within the groove on the occluder. By pulling on the collet tube with the occluder firmly secured, the device can be returned to its collapsed state and retrieved into the delivery assembly. From this point the delivery process can be restarted.

Figure 30:
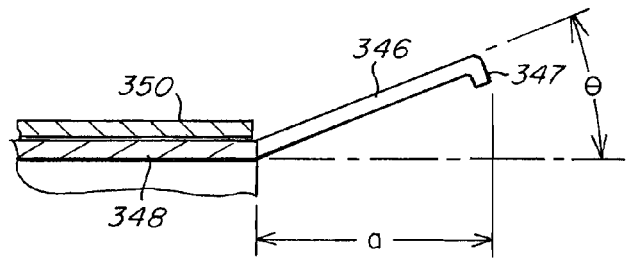
FIG. 30 is a detail view of the collet finger according to one aspect of the disclosure.

FIG. 30 illustrates a detail view of a collet finger 346 and the collet sheath 350. The collet finger 346 is configured to be about 20 degrees from the base of the collet finger 346, the dimension identified as $\theta$ in FIG. 30. The collet finger 346 can extend from the collet tube 348 approximately 0.25 in., the dimension identified as "a" in FIG. 30. The distance "a" can be from 0.1 in. to 0.5 in. The angle $\theta$ can vary from low single digits to approximately 70 degrees. In general, as the length of "a" is decreased, the angle desired for $\theta$ would increase. The collet finger 346 includes a radially inwardly extending protrusion 347, which is formed by a bend in the nitinol finger. The bend is preferably 90 degrees and the dimensions of the protrusion are selected to securely fit within the groove 314. As illustrated in FIG. 20, supra, the groove 314, for example, could be 0.02-0.04 in. in axial length and 0.005-0.020 in radial depth. The groove 314 is illustrated as a circumferential groove; alternatively, recesses can be formed in part of the occluder 310 to receive the collet fingers 346. It is preferable that the collet fingers 346 have a close fit but not an interference fit in the axial direction. This assures that the collet system can move the device without significant slippage. It is also preferable that the protrusion does not come into contact with the bottom of the groove 314 (the inner-most radial surface). This assists the deployment of the occluder.

Figure 31:
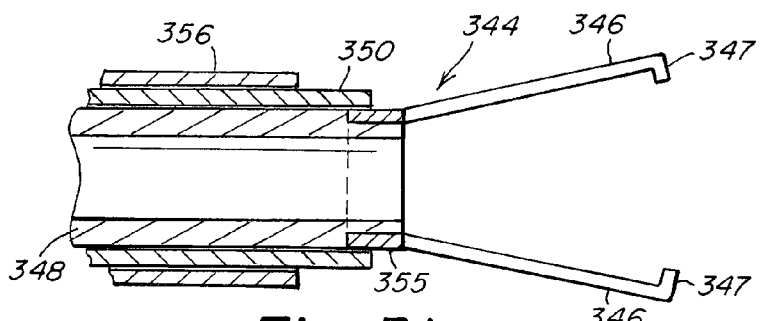
FIG. 31 is a detail cross-sectional side view of the collet system in the splayed configuration.
Figure 32A:
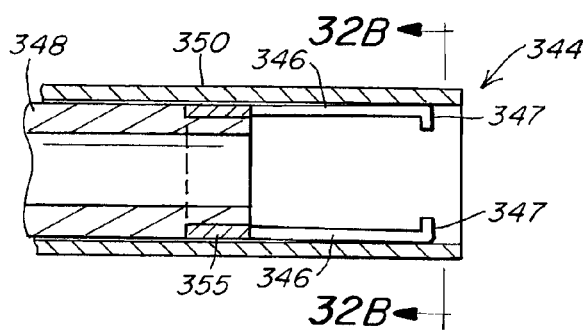
FIG. 32A is a detail cross-sectional view of the collet system in the constrained configuration.
Figure 32B:
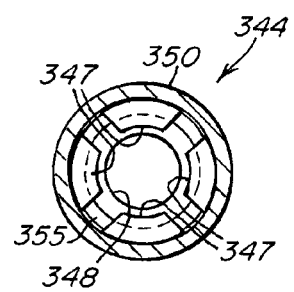
FIG. 32B is a cross-section taken along lines 32B-32B in FIG. 32A.

FIGS. 31, 32A, and 32B illustrate alternative embodiments of the second securement system. The fingers are formed by cutting sections from a nitinol hypotube that has, for example, a 0.0075 in. wall thickness. The inner diameter could be, for example, 0.098 in. and the outer diameter could be 0.117 in. The thickness of the hypotube could be as large as 0.050 in. or more. Nitinol is a desirable material due to its superelastic characteristics. Other superelastic materials or simply springy material may be used. Of course, the materials would have to be suitable for use in a medical device. The nitinol hypotube is cut so that the fingers extend from one side and the hypotube ring is uncut at the other end. As an example, FIG. 31 illustrates a cross section where the hypotube is disposed on an end of the collet tube 348. The nitinol ring 355 is disposed on the outside surface of the collet tube. The nitinol ring 355 may be affixed to the collet tube 348 by a variety of known techniques such as a suitable adhesive.

FIGS. 32A and 32B illustrate the side and end view of representative collet fingers 346. In a preferred embodiment, there are four collet fingers 346 that are used to secure the occluder in the delivery system. In alternate embodiments, there may be as few as two collet fingers 346 or as many as 8. One practical limitation is the circumferential size of the collet fingers 346 and the rigidity of the collet fingers 346 as they are used to deploy the occluder. In the embodiment illustrated in FIG. 32B, the four collet fingers 346 are formed by cutting away a ⅛th section of the cross section and forming four equally spaced collect fingers 346. During the formation process the roundness of the collet finger 346 along the circumference can be modified to adjust the bendability of the collet fingers 346.

Figure 33:
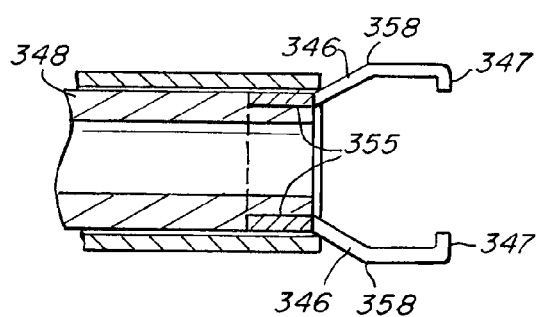
FIG. 33 is a detail sectional view of another embodiment of the collet system according to the disclosure.

FIG. 33 illustrates another embodiment of the collet fingers 346. In this embodiment, the collet fingers 346 include a bend 358 between the base ring 355 and the protrusion 347. As illustrated the bend 358 is in the approximate halfway between the base ring 355 and the protrusion 347. The bend 358 can be almost any configuration but the bend 358, as illustrated, allows for force to be applied to the occluder and have the configuration of the collet fingers 346 be such that it does not extend the so far away from the collet tube 348 in the radial direction. This allows the occluder to have a more controlled delivery because of the increased forces applied and a more compact system because the collet fingers 346 do not extend radially away from the collet tube 348 as far.

Figure 34:
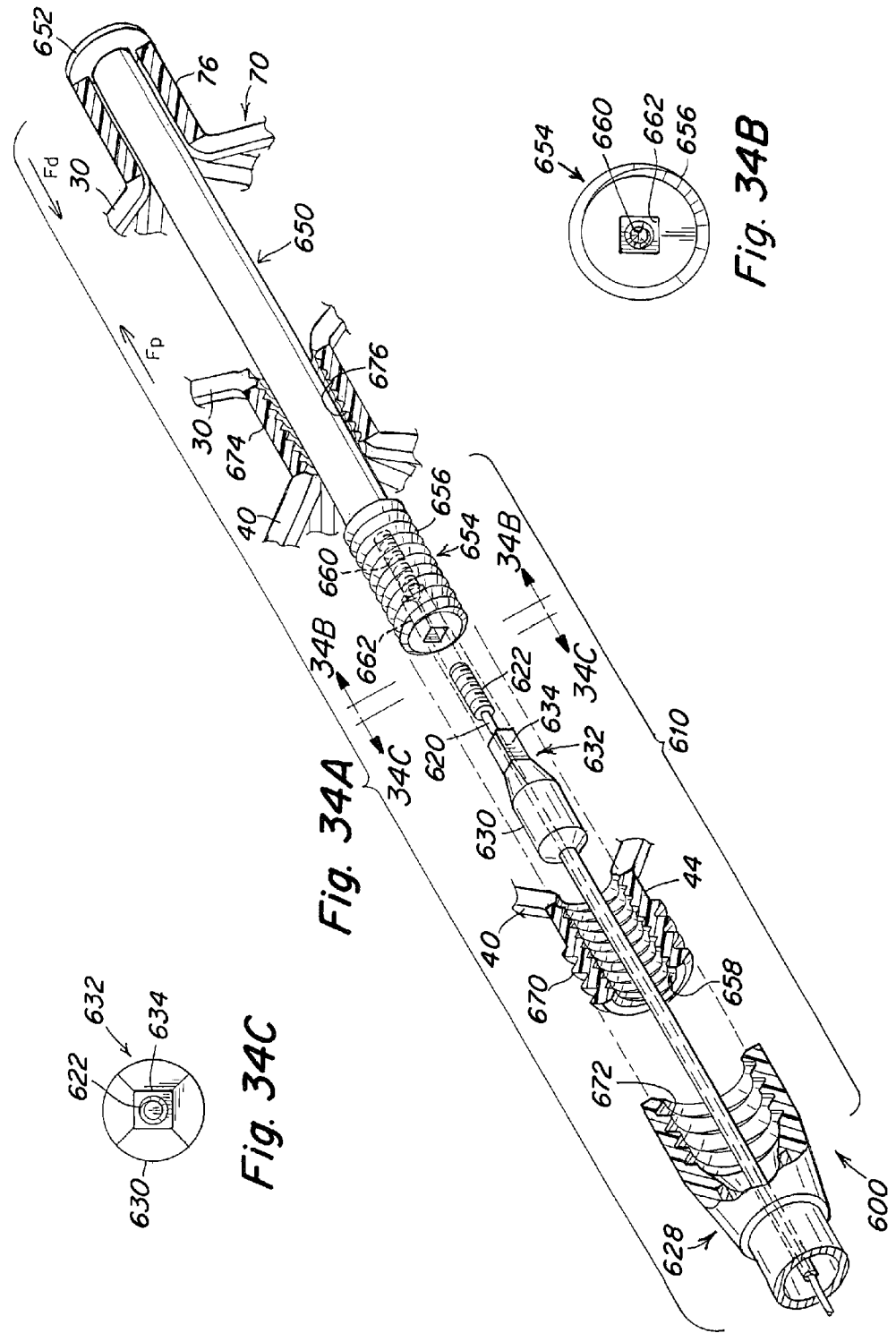
FIG. 34A is an exploded perspective view of an occluder delivery system.
FIGS. 34B and C are cross-sectional views of the catch system shown in FIG. 34A.

FIGS. 34A-C illustrate an alternative embodiment 600 of an occluder delivery system using a delivery wire with an alternative second securement system. In this embodiment, the proximal end of the catch element screws onto the proximal end of the occluder to secure it at a deployed configuration. FIG. 34A is an exploded perspective view of a catch member 650 and first securement system 610. Catch member 650 can be disposed in the radially central portion of the occluder 70, and includes a distal flange 652, a proximal end 654, and a catch body 656. The flange 652 rests against the distal end of the occluder 76 as described above, for manipulating the occluder 70 during delivery and/or retrieval and for catching the occluder 70 in the deployed position. The distal end of the catch member 650 is allowed to rotate freely relative to the occluder 70, as described below. The proximal end 654 of the catch member 650 includes external threads 656 that cooperate with internal threads 658 on the occluder proximal end 44. When engaged, the threaded connection operates to hold the occluder in the deployed configuration and the catch mechanism thereby provided can be released by unscrewing external threads 656 from internal threads 658. The proximal end 654 of the catch member also includes internal threads 660 and a slot 662 (shown in dotted lines), disposed at the radial center. The internal threads 660 are designed to cooperate with external threads 662 on the distal end of the delivery wire 620. When engaged, this threaded connection allows movement of the delivery wire 620 to move and position the catch member 650, e.g., by the application of force Fd or FP The inner catheter 630 can freely slide within the delivery catheter 628 and can freely rotate. Delivery catheter 628 threadably engages external threads 670 on the occluder via internal threads 672.

Disposed at the distal end 632 of the inner catheter is a key 634 that can be inserted into slot 662 at the proximal end 654 of the catch member. Key 634 fits into slot 662 such that rotating the inner catheter 630 causes the catch member 650 to be rotated, in order to threadably engage or disengage threads 658 on the proximal end of the occluder with threads 656 on the proximal end of the catch member. The key 634 and slot 662 provide the mechanism for threadably engaging or disengaging the proximal end 654 of the catch element from the occluder 70.

At connection member 674, the occluder may also include an additional inner threaded portion 676 that can cooperate with threads 656 to hold the occluder in an intermediate position.

FIGS. 34B and 34C are sectional views of the catch system used in FIG. 34A, along lines K1, and K2, respectively. Although the cross-section of the key 634 and the slot 662 are shown as squares, a variety of cross-sections could be used.

Another embodiment of the second and first securement system of the delivery system, illustrated in FIGS. 35-38, uses a filament instead of a delivery wire. As shown in FIG. 35, the second securement system 340 is illustrated as the collet system 344, which is largely the same as in the previous embodiment. Of course, other securement systems included a threaded connection can be used. The first securement system includes an eyelet 510 around which a flexible filament 512 can be fastened or looped. The flexible filament can be a suture thread (monofilament or polyfilament), a thin metallic wire or other flexible material that can withstand a tension load.

Figure 37:
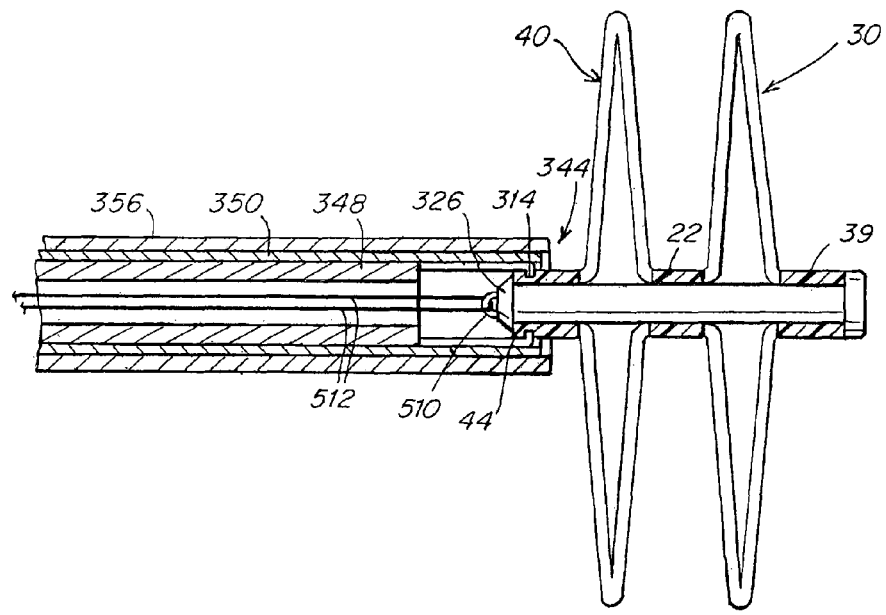
Figure 38:
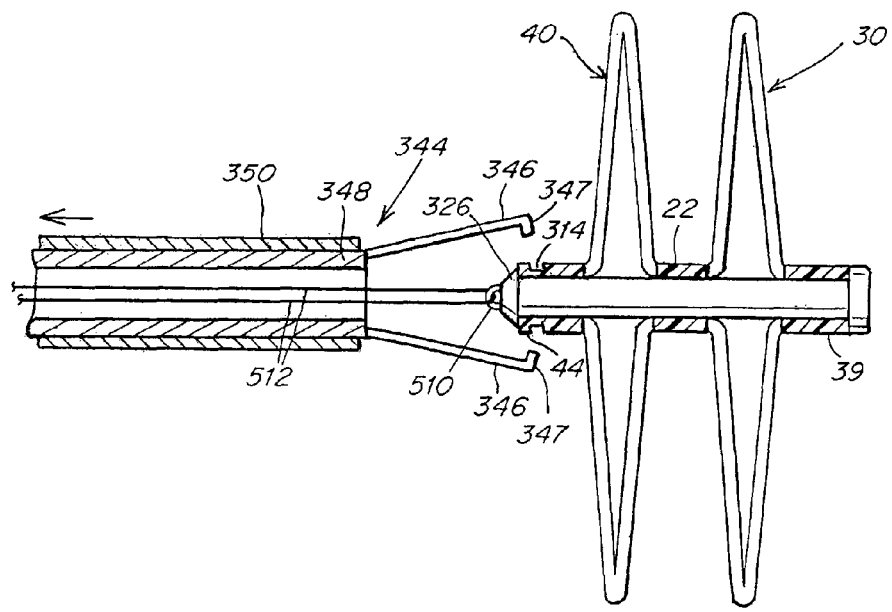

The deployment of the occluder is effected by withdrawing the delivery sheath 356 to expose and let the distal petals 30 on the distal side of the occluder expand as illustrated in FIG. 36. Once the distal petals 30 are deployed by the catch element 326, the delivery sheath 356 is further withdrawn proximally and the proximal petals 40 are exposed as illustrated in FIG. 37. The filament is pulled to cause the catch element secures the occluder at deployed configuration. Once the catch element secures the occluder in the deployed configuration, the collet system is released in the manner described above and illustrated in FIG. 38. Once the collet system is released, the position may be evaluated. If the position is satisfactory, filament 510 is pulled through the eyelet and removed from the body. Either a delivery wire, a tube or filament is appropriate for the first securement system depending on the design considerations. For example, if the occluder in the delivery configuration lacks sufficient stiffness to allow the delivery sheath been pulled back without affecting the position of the device in the delivery system, a delivery wire that has some stiffness would be more desirable.

Figure 39A:
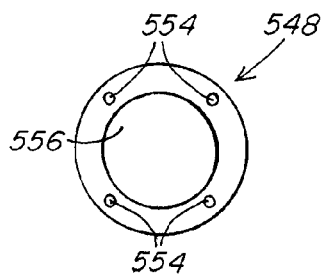
FIG. 39A is a front cross-sectional view of a delivery catheter according to one embodiment of the disclosure.
Figure 39B:
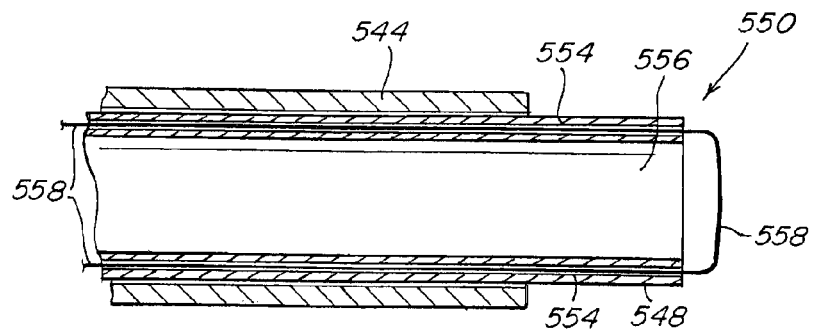
FIG. 39B is a side cross-sectional view of a delivery catheter with sutures according to one embodiment of the disclosure.
Figure 39C:
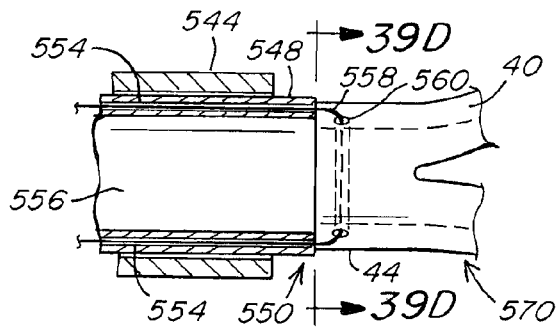
FIG. 39C is an elevational view of a delivery catheter with sutures secured to an occluder according to one embodiment of the disclosure.
Figure 39D:
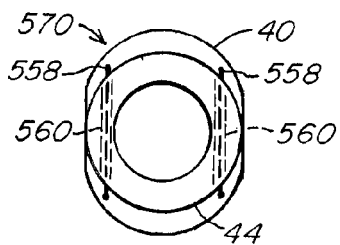
FIG. 39D is an elevational end view of delivery catheter along lines 39D of FIG. 38C.
Figure 40:
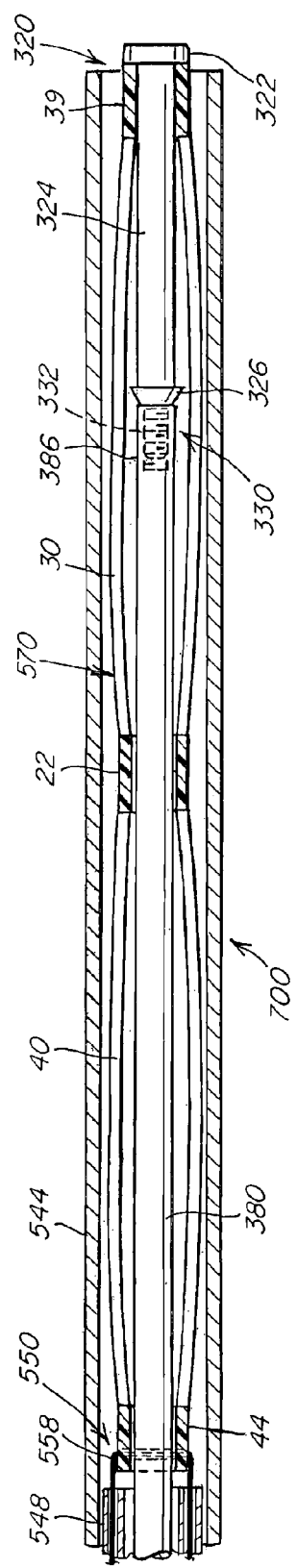
FIG. 40 is a sectional view of a delivery assembly during a step in the deployment process according to one aspect of the disclosure.

An alternative embodiment of the second securement system is illustrated in FIGS. 39-40. FIG. 39A illustrates an end view of the construction of the delivery catheter 548 with suture second securement system. The delivery catheter 548 a central lumen 556 and secondary lumens 554 surrounding the central lumen 556. The outer lumens 554 are used to provide a passageway for containing sutures 558 secured to the occluder 570, illustrated in FIG. 39C, as the attachment mechanism for the second securement system 340 and passed through the delivery catheter 548 to the user for manipulating the second securement system. Although four outer lumens 554 are shown, any number of lumens may be provided suitable for use in the delivery system 340. A sufficient number of sutures 558 should be provided in order to securely attach the occluder 570 and permit the necessary operations. The sutures 558 are shown in FIG. 39B, which illustrates sheath delivery 544 which contains delivery catheter 548. Referring again to FIG. 39C, the delivery catheter 548 is connected to the proximal end 44 of the occluder 570 via the sutures 558 which attach to holes 560 provided in the occluder 570. The sutures 558 are threaded through the holes 560 and can be readily detached by, e.g., cutting the sutures and pulling through the delivery catheter 548. Attachment of the sutures 558 to the occluder 570 may be provided in a number of ways, such as providing hooks or a flange on the occluder 570, around which the sutures can be wrapped or fastened, or wrapping the sutures 558 around the proximal petals 42. The sutures 558 can also be embedded into the proximal end 44 of the occluder 570. The flexible filament used to provide the thread can be a suture thread (monofilament or polyfilament), a thin metallic wire or other flexible material that can withstand a tension load.

The recovery process for a device in which the suture second securement (e.g., collet) system is described below. When the suture second securement has been disengaged and a retrieval capability is desired, additional filaments can be attached to the proximal tip of the occluder. For example, with reference to FIG. 35, filaments 514 are attached to the proximal end 44 of the occluder 570 through holes 516. The filaments 514 can be attached in a variety of locations, for example, they can be looped around one of the proximal loops on the proximal side of the device. When the filaments 514 are provided, the clinician would orient the delivery catheter 548 (as illustrated in FIG. 39B) to the proximal end 44 of the occluder 570 and then pull on the filaments 514 to uncatch the system so that the profile of the device can be reduced and reinserted into the delivery catheter. In an embodiment where the filament 514 is present and the device is deployed satisfactorily, the filaments 514 can be cut or otherwise withdrawn from the body.

FIG. 40 illustrates a complete delivery assembly 700 with the occluder 570 in place for delivery and deployment at the deployment site. As shown, the occluder 570 is in its elongated, low profile configuration. The occluder 570 is secured at its distal end 39 by the first securement system 330 to the delivery wire 380 and at its proximal end 44 by the second securement system 550 to the delivery catheter 548. The occluder 570, delivery wire 380 and delivery catheter 548 are contained within the sheath 544. The occluder 570 can be detached from the first securement system 330 by unscrewing the delivery wire 330, which is connected by threaded portion 386 to threaded portion 332. The occluder 570 can be detached from the second securement system 550 by removing the sutures 558, for example, by pulling on them from the user end of the delivery system.

Figure 41:
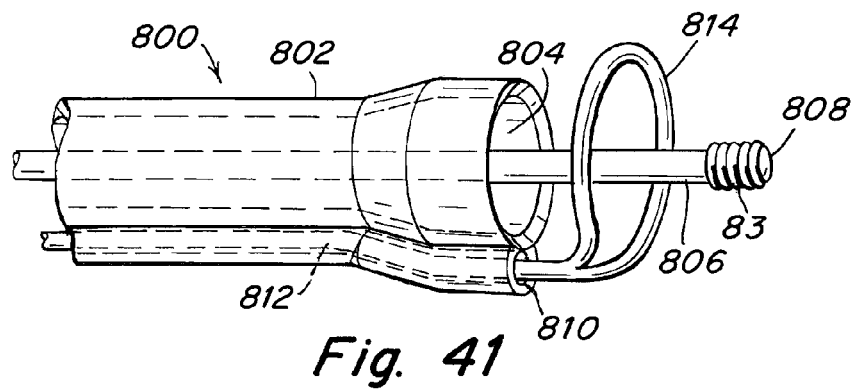
FIG. 41 is a close-up perspective view of the catheter portion of a delivery assembly according to an aspect of the disclosure.
Figure 42:
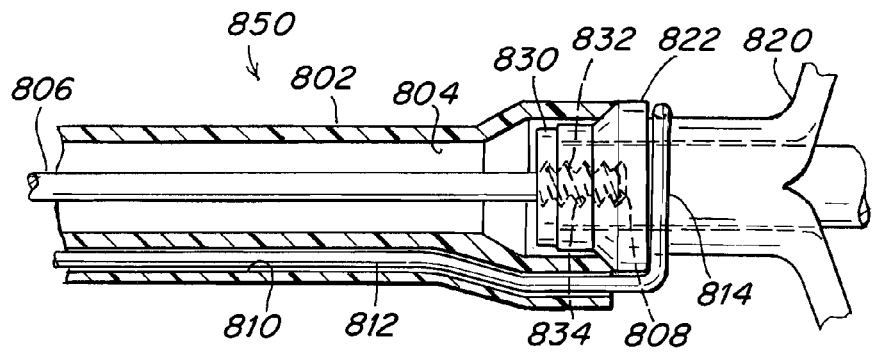
FIG. 42 is a cross-sectional side view of a delivery assembly using the catheter portion shown in FIG. 41.

FIGS. 41 and 42 illustrate an alternative embodiment 800 of an occluder delivery system for occluder 820 and catch member 830, employing an alternate second securement system. FIG. 41 shows a close-up view of the distal end of the catheter portion 800 of the delivery system 850. Delivery catheter 802 is a dual-lumen catheter that comprises a first, center lumen 804 and a second side lumen 810. A delivery wire 806 is contained in the center lumen 804. The delivery wire 806 includes an internally threaded portion 832 on its distal end 808. The internally threaded portion 832 cooperates with an externally threaded portion 834 on catch member 830 to form a threaded connection that provides a first securement system, as discussed with reference to FIG. 8, for example. Although the embodiment illustrated in FIGS. 41 and 42 incorporates this threaded first securement system, any first securement system that provides the needed delivery, deployment and/or retrieval features may be used with the second securement system illustrated in FIGS. 41 and 42. In particular, first securement systems shown in FIGS. 24, 25A-B, 26A-B, 27A-B and attachment 510-512 in FIG. 35-36 above, FIGS. 18A-C of U.S. application Ser. No. 11/729,045, and the description in paragraph [0068] of U.S. application Ser. No. 11/729,045 may all be suitable for certain embodiments. In addition, combinations of first and second securement systems discussed herein can be used with various configurations of an occluder having the basic tubular construction described herein, such as disclosed in U.S. application Ser. Nos. 10/890,784, 11/111,685, 11/395,718, 11/729,636 and 11/728,694. The applications mentioned in this paragraph have the same assignee as the present application and are incorporated herein by reference in their entirety.

According to one embodiment of the invention, as illustrated in FIG. 41, a snare wire 812 runs through the side lumen 810. The snare wire 812 terminates in a snare loop 814 used to snare the proximal end of an occluder frame 822 by hooking over the end. The proximal end of the occluder frame 822 may include a flange, a lip, hook, flared shape or other feature that permits the loop 814 to snare the end. In certain embodiments, the loop 814, upon exiting catheter lumen completely, has a larger diameter than the proximal end of the occluder frame 822 and can be released by turning and pulling the loop 814 over the end of the occluder frame.

FIG. 42 shows the catheter portion 800 connected to an occluder frame 820 in a stage of the occluder deployment. During deployment, the outer sheath is withdrawn, exposing the attached occluder frame 820. With the snare device holding the occluder frame 820 tight, and the dual-lumen catheter 802 being kept steady, the delivery wire 806 can be used to pull the catch member 830 proximally until the occluder 820 is deployed and locked into its deployed configuration. Alternatively, the occluder 820 can be deployed by pushing the dual-lumen catheter 802 in the distal direction and holding the delivery wire 806 and the snare loop 814 steady. During release, either second securement system, via the snare loop 814, or the first securement system, via the threaded portion 834, can be released first, while the other is held secure. The threaded portion 834 is released by unscrewing the connection. The snare second securement is released by allowing the snare loop 814 exiting its catheter lumen completely and therefor loosen around the occluder frame 820, either by advancing the snare wire 812 distally while keeping dual-lumen catheter 802 steady or by withdrawing the dual-lumen catheter 802 proximally while holding snare wire 812 steady. This allows the snare loop 814 to then be pulled over and off the proximal end of the occluder frame 822. Upon release of either attachment mechanism, the position of the deployed occluder can be assessed. If necessary, the released attachment mechanism can be reattached to retrieve the deployed occluder. The snare loop 814 can be reattached by advancing the snare wire 812 until the occluder frame 820 is caught in the loop, and then snare wire 812 is pulled proximally to withdrawn snare loop 814 at least partially into its catheter lumen and thus hold the occluder frame 822 in place. The delivery wire 806 can be reattached as described hereinabove.

The snare device, including snare wire 812 and snare loop 814, could be made of a single wire, multi-strand wire, single or multi-looped wire or any combination thereof. Although Nitinol is the preferred material choice for the snare device, any other material that is suitable for the application may be used. The distal portion of the snare wire 812, including snare loop 814 may be coated, printed or wrapped with radiopaque material, such as gold, tungsten or platinum.

The distal loop 814 of the snare device, upon exiting its catheter lumen complete, is sized to fit and be slightly larger than the profile of the proximal end of the occluder frame 822, and designed for the purpose of ease of use. During release, the snare device is advanced in the distal direction so that its entire distal loop 814 comes out of the distal end of the side lumen 810. Because the size of the entire snare loop 814 is greater than the size of the proximal end of the occluder frame 822, the loop 814 releases over the end 822 and the occluder frame 820 is released. Preferably, the snare loop 814 is designed so that it swivels proximally as it is coming out of the distal end of the side lumen 812. By swiveling proximally, it releases more readily and clearly and reduces the possibility of the loop 814 hanging on the end of the occluder frame 820 in a way that would hinder its release. One advantage of this securement system is that it is relatively simple to release and attach. It also requires less movement than certain other types of securement systems, such as threaded connections.

Figure 43:
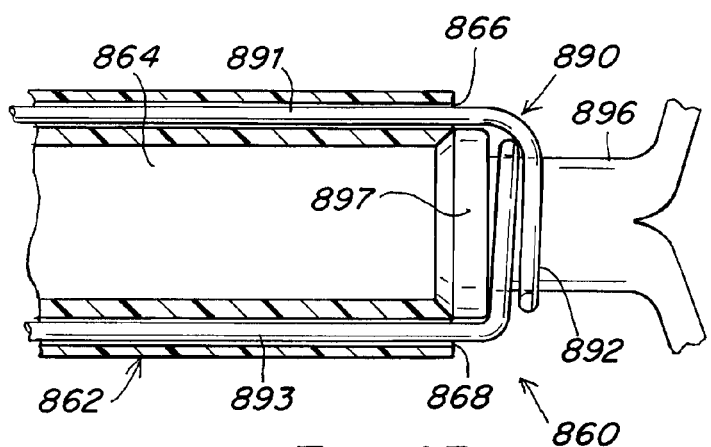
FIG. 43 is a cross-sectional side view of a delivery assembly using a catheter portion with a coiled snare according to one aspect of the disclosure.

FIG. 43 illustrates a portion of a delivery system 860 for an occluder 896 that uses an alternate embodiment of a snare-type second securement system. Catheter 862 is a tri-lumen catheter that includes a center lumen 864, a first side lumen 866, and a second side lumen 868. Delivery wire 806, not shown, is contained in the center lumen 864. A snare 890 includes an first snare wire 891, a snare coil 892, and a second snare wire 893. Instead of a terminal loop, the first snare wire 891 of snare 890 turns into a snare coil 892 that wraps around a flange 897 on the occluder frame 896, which then continues to become the second snare wire 893. The first snare wire passes 891 passes through the first side lumen 866 and the second snare wire 893 passes through the second side lumen 868. Because it uses a coil 892 instead of a fixed loop, the opening can loosen and tighten. When the snare 890 is advanced distally, the coil 892 opens up and releases the occluder 896. In one embodiment of the invention, the second snare wire 893 passes back to the control portion of the catheter, and thus both snare wires 891 and 893 can be used to manipulate the snare coil 892. In another embodiment, the second snare wire 893 is fixed to the catheter, and thus only snare wire 891 is used to manipulate the snare coil 892.

Figure 44A:
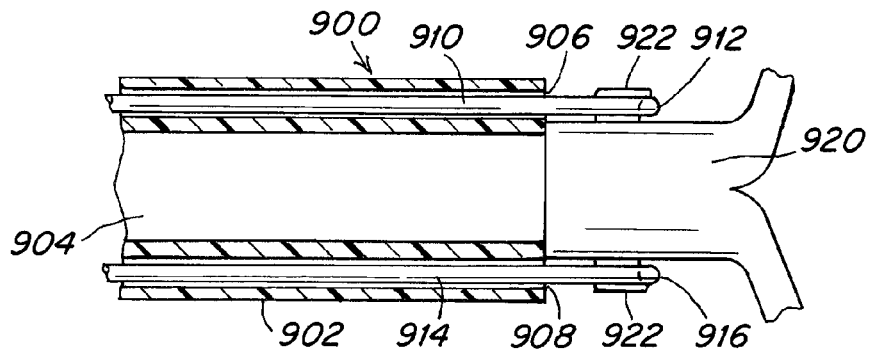
FIG. 44A is a cross-sectional side view of a delivery assembly using a catheter portion with a double snare according to one aspect of the disclosure.
Figure 44B:
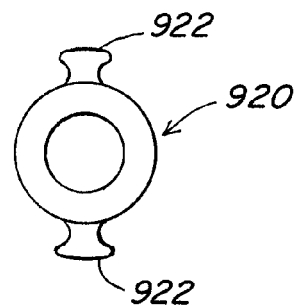
FIG. 44B is an end view of the proximal end of an occluder for use with a double snare according to one aspect of the disclosure.
Figure 44C:
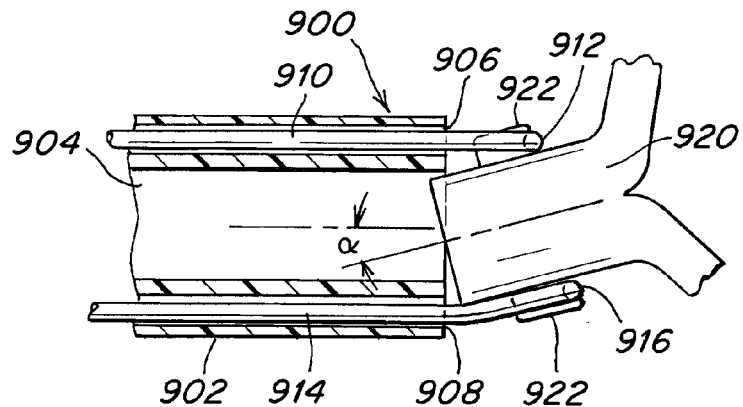
FIG. 44C is a cross-sectional side view of a delivery assembly using a catheter portion with a double snare according to one aspect of the disclosure.

FIG. 44A illustrates a portion of a delivery system 900 for an occluder 920 that uses an alternate embodiment of a snare-type second securement system. This embodiment uses two snares. The catheter 902 is a tri-lumen catheter that includes a center lumen 904, a first side lumen 906 and a second side lumen 908. Delivery wire 806, not shown, is contained in the center lumen 904. First side lumen 906 contains first snare wire 910. First snare wire 910 terminates in a snare loop 912. Second side lumen 908 contains second snare wire 914. Second snare wire 914 also terminates in a snare loop 916. The snare loops 912 and 916 catch on protrusions 922 formed on the occluder frame 920. Protrusions 922 are further illustrated in FIG. 44B, which is an end view of the occluder frame 920. Using two snare wires 910 and 914 allows force to be evenly applied to the occluder 920 from either side, which improves the alignment and reduces the likelihood of distortion in the connection between the occluder 920 and the catheter 902. According to some embodiments of the invention, this embodiment of snare second securement allows the catheter 902 and the occluder 920 to bend at an angle relative to each other, and be adjusted either actively or passively. FIG. 44C illustrate how the snare loops 912 and 916 continue to hold the occluder frame 920 in place even when the catheter 902 is bent at an angle □ relative to the longitudinal axis of the occluder frame 920. In one embodiment, the angle might be altered by applying tension to one of snare wires 910 or 914. The snare wires 910 and 914 may have elasticity to enhance this feature. In some embodiments, the shape of the interface between the proximal end of the occluder frame 920 and the distal end of the catheter 902 could be modified. For example, the connection could be similar to a ball-and-socket connection.

Figure 45A:
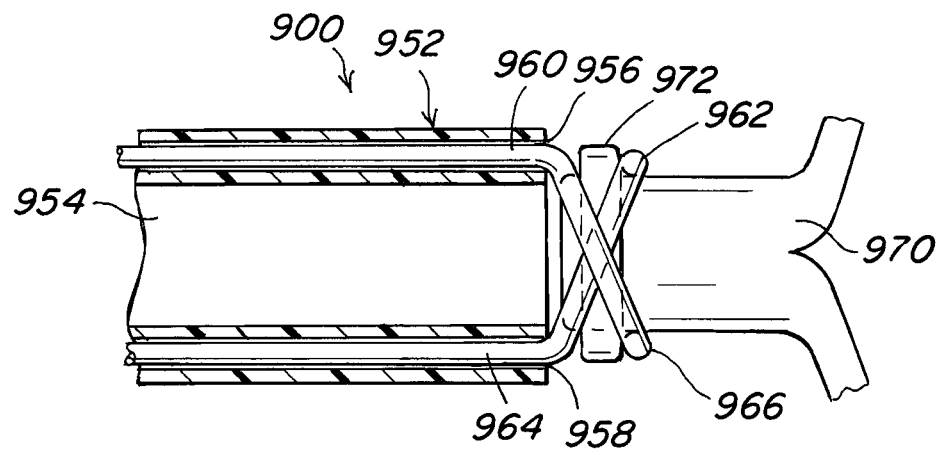
FIG. 45A is a cross-sectional side view of a delivery assembly using a catheter portion with a criss-cross double snare according to one aspect of the disclosure.
Figure 45B:
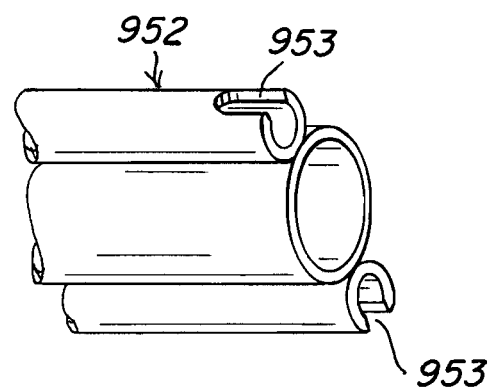
FIG. 45B is a perspective view of the distal end of a catheter for a double snare.

FIG. 45A illustrates a portion of a delivery system 950 for an occluder 970 that uses an alternate embodiment of a snare-type second securement system with two snares. The catheter 952 is a tri-lumen catheter, including a center lumen 954, a first side lumen 956 and a second side lumen 958. Delivery wire 806, not shown, is contained in the center lumen 954. A first snare wirer 960 passes through the first side lumen and a second snare wire 964 passes through the second side lumen. First snare wire 960 terminates in a first snare loop 966 and second snare wire 964 terminates in a second snare loop 962. The snare loops 964 and 966 criss-cross over the end of the occluder frame 970 and are held in place by flange 972. First snare wire 960 passes through the first side lumen 956, which is oriented at the top of the illustration in FIG. 45A, and the first snare loop 966 crosses over to snare the opposite side of the occluder frame 970. Second snare wire 964 passes through the second side lumen 958, which is oriented at the bottom of the illustration in FIG. 45A, and the second snare loop 962 crosses over to snare the opposite side of the occluder frame 970. The use of two snares provides a secure hold, reduces the potential for distortion by holding the occluder 970 from both sides and balancing the forces applied on each side, and also enables the occluder 970 to be manipulated by actively or passively applying different forces to each snare wire 960 or 964. The criss-cross snare also prevents rotation of the occluder frame 970 when the delivery wire 806 is released by unscrewing it from the catch member. Flange 972 of the occluder can be an annular flange that extends all the way around the proximal end of the occluder frame 970 or may extend only part way around, sufficient for the snare loops 962 and 966 to catch at the correct locations. The snare loops 962 and 966 may be released by advancing the catheter distally until the loops 962 and 966 slacken around the flange 972 and bend outward or rotate proximally and can be retracted into the catheter 952. As shown in FIG. 45B, in some embodiment, the side lumens 956 and 958 and the outer covering of the catheter 952, if any, may include slots 953 at the distal end to allow the loops 962 and 966 to rotate proximally and then retract into the catheter 952. The loops 962 and 966 may also rest in the slots 953 after delivery.

The embodiments and techniques described here are described preferably for use with a device made of a polymer and formed from a single tube, such that the tube is a single monolithic material. The catch mechanism can be all or partly monolithic or integral with the tubular structure, or there can be an absence of any type of bonding or rigid connection to the rest of the tubular structure, in which case there may be some spring force or other force that holds the locking mechanism in place. While the device is thus shown as being substantially formed from a single tubular body, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

While the description above refers to strings, filaments, sutures and wires, and while the term "wire" might convey a more rigid piece than a string, a suture or a filament, all these terms are essentially interchangeable, and further include embodiments in which the wire, string, suture or filament is a hollow tube or conduit to allow another wire, as needed, to pass through its longitudinal axis. Each wire, string, suture and filament can be composed of one or more wires, strings, sutures and filaments.

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

Having described various embodiments of the invention, it should be apparent that various modifications be made without departing from the spirit and scope of the disclosure.

What is claimed is:

1. A delivery system to deliver a medical device through a body lumen comprising:
    a securement system comprising a first snare wire that is securable to an end portion of the medical device, and a second snare wire that is securable to the end portion of the medical device, wherein the first and second snare wires are operable to release the medical device at a deployment location, and wherein the first snare wire and the second snare wire are independently adjustable to position and release the medical device at the deployment location; and
    a delivery sheath comprising a center lumen that encloses at least a portion of the medical device, a first side lumen that contains the first snare wire, and a second side lumen that contains the second snare wire, and wherein the first side lumen and the second side lumen each comprise an external slot extending from a distal tip partially along a length of each side lumen.

2. The delivery system of claim 1, wherein the medical device is an occluder.

3. The delivery system of claim 1, wherein the first and second snare wire is at least one member selected from the group of a wire, tube, or solid elongated member and filament.

4. The delivery system of claim 1, wherein the first and second snare wire comprises at least one member selected from the group consisting of metal, alloy, stainless steel, MP35N alloy, polymer, memory metal, and nitinol.

5. The delivery system of claim 1, wherein the first and second snare wires are configured to attach to at least one protrusion on the medical device.

6. A delivery system to deliver a medical device through a body lumen comprising:
    a securement system comprising a first snare wire that is securable to a protrusion on an end portion of the medical device, and a second snare wire that is securable to a protrusion on the end portion of the medical device, wherein the first and second snare wires are operable to release the medical device at a deployment location, and wherein the first snare wire and the second snare wire are independently adjustable to position and release the medical device at the deployment location; and
    a delivery sheath comprising a center lumen that encloses at least a portion of the medical device, a first side lumen that contains the first snare wire, and a second side lumen that contains the second snare wire, and wherein the first side lumen and the second side lumen each comprise an external slot extending from a distal tip partially along a length of each side lumen.

7. The delivery system of claim 6, wherein the medical device is an occluder.

8. The delivery system of claim 6, wherein the first snare wire is securable to a first protrusion on the end portion of the medical device, and the second snare wire that is securable to a second protrusion on the end portion of the medical device.

9. The delivery system of claim 8, wherein the protrusions are on opposite sides of the end portion of the device.

* * * * *